United States Patent

Nakano et al.

Patent Number: 5,981,420
Date of Patent: Nov. 9, 1999

[54] OXIDATION CATALYTIC SYSTEM AND OXIDATION PROCESS

[75] Inventors: Tatsuya Nakano, Himeji; Yasutaka Ishii, Takatsuki, both of Japan

[73] Assignees: Daicel Chemical Industries, Ltd.; Yasutaka Ishii, both of Osaka, Japan

[21] Appl. No.: 09/024,514

[22] Filed: Feb. 17, 1998

[30] Foreign Application Priority Data

Feb. 17, 1997 [JP] Japan ..................... 9-032437
Dec. 22, 1997 [JP] Japan ..................... 9-353396

[51] Int. Cl.$^6$ ..................................... B01J 31/00
[52] U.S. Cl. ................. 502/155; 502/162; 502/204; 502/213; 562/549; 562/409; 568/357; 568/431; 568/836
[58] Field of Search ................. 502/150, 152, 502/153, 154, 155, 156, 162, 163, 204, 206, 207, 209, 210, 211, 215; 562/549, 409; 568/357, 431, 836

[56] References Cited

U.S. PATENT DOCUMENTS 5,705,685  1/1998  Lyons et al. ................. 562/549

FOREIGN PATENT DOCUMENTS 4216621   9/1942  Japan .
02019336  1/1990  Japan .
08038909  2/1996  Japan .

OTHER PUBLICATIONS

Lecture Draft II, 67$^{th}$ Spring Annual Meeting of Chemical Society of Japan (1994) and English translation of relevant parts.
Derwent Publications Ltd., London, GB, AN 76-01006X, Section Ch, Week 7601, XP002067318, and JP 50 116 443A. (Abstract only) (1975).
Sakaguchi et al., Technology Reports of Kansai University, No. 38, pp. 123–131, XP002067301, Osaka, Japan (Mar. 1996).
Iwahama et al., Tetrahedron Letters, vol. 36, No. 38, pp. 6923–6926 (1995).
Ishii et al., Journal of Organic Chemistry, vol. 61, pp. 4520–4526, XP002067302 (1996).

Primary Examiner—Shailendra Kumar
Assistant Examiner—Sreeni Padmanabhan
Attorney, Agent, or Firm—Birch, Stewart, Kolasch & Birch, LLP

[57] ABSTRACT

A substrate (e.g., a cycloalkane, a polycyclic hydrocarbon, an aromatic compound having a methyl group) is oxidized with oxygen in the presence of an oxidation catalytic system comprising an imide compound of the following formula (1) (e.g., N-hydroxyphthalimide) and a co-catalyst containing a element selected from Group 3 to 12 elements (in particular, Group 4 to 11 elements) of the Periodic Table of Elements. The co-catalyst comprises a compound containing plural elements (except heteropolyacid and a combination of Group 7 and 8 elements of the Periodic Table of Elements), and is useful for the formation of an oxide (e.g., a ketone, an alcohol, a carboxylic acid):

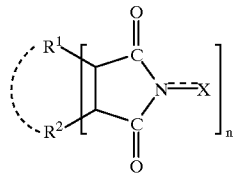

(1)

wherein $R^1$ and $R^2$ represent a substituent such as a hydrogen atom or a halogen atom, or $R^1$ and $R^2$ may together form a double bond or an aromatic or nonaromatic 5- to 12-membered ring, X is O or OH, and n is 1 to 3.

12 Claims, No Drawings

OXIDATION CATALYTIC SYSTEM AND OXIDATION PROCESS

FIELD OF THE INVENTION

This invention relates to a complexed oxidation catalytic system, which is useful for oxidation of a substrate with oxygen, to an oxidation process using the catalytic system, and to a process for producing an oxide (a ketone, an alcohol, an aldehyde or a carboxylic acid).

BACKGROUND OF THE INVENTION

An oxidation reaction is a basic reaction in the field of industrial organic chemistry, and there are a variety of known oxidation processes, in particular an oxidation process for a substrate using nitric acid. By way of illustration, adipic acid that is a raw material for the production of nylon 66 is prepared by a process of oxidizing cyclohexanol and no other, or a mixture of cyclohexanol and cyclohexanone (K/A oil) with nitric acid. An aromatic compound having a carboxyl group (e.g., benzoic acid) has been produced by a process that comprises oxidizing an aromatic compound having a methyl group (e.g., toluene) with nitric acid or dichromic acid.

Each of these processes, however, requires an expensive exhaust gas treatment plant for treatment of $N_2O$ and $NO_x$ produced by the oxidation with nitric acid. Similarly, the case with dichromic acid requires treatment of a chromium component.

Polycyclic hydrocarbons each having a functional group in a bridgehead position are compounds applicable to many applications, and most of these compounds may be induced or derived from corresponding alcohols. In particular, polyols each substituted with hydroxyl groups on plural, i.e., two or more bridgehead positions can be advantageously employed for production of progressive materials (highly functional materials). However, it is difficult to introduce hydroxyl groups into the bridgehead positions of such chemically stable polycyclic hydrocarbons with effectiveness and high efficiency. By way of illustration, introduction of hydroxyl groups is conducted by bromination of a bridged cyclic hydrocarbon (e.g., adamantane or its derivative) with the use of excess bromine (e.g., 10 times by mole or more), and hydrolyzing the formed bromide with silver nitrate or silver sulfate in an excess amount greater than a stoichiometric amount (Chem. Ber., 92, 1629 (1959), 93, 226, 1161 (1960): J. Org. Chem., 26 2207 (1961)).

In this process, however, the reaction should be conducted over a long period at a temperature of about 100° C. using a large quantity of bromine. Besides, the reaction consumes the expensive silver reagent in a large quantity. Moreover, successive bromination of two or more bridgehead positions would not be expected. In addition, since an adamantanetriol cannot be formed directly from adamantane, it has to be produced by isolation and hydrolysis of a successively highly brominated compound. Accordingly, the yield of the adamantanetriol is extremely low at about 10 to 30% [Tetrahedron Letters, 19 1841 (1967); Just. Liebigs Ann. Chem., 717 60 (1968)].

As a process for producing an adamantanediol, Japanese Patent Publication No. 16621/1967 (JP-B-42-16621) discloses that an adamantanediol is obtained by reacting adamantane with five times by mole or more of chromic acid in a concentrated acetic acid solution. However, in this technology, for a treatment of chromic component is needed, and in addition, although an adamantanediol is formed according to the process, oxidation of adamantane to a triol or higher polyol will not proceed, even when the reaction is carried out in severe conditions.

From the viewpoints of resource and environment, a preferable oxidation process is a catalytic oxidation in which molecular oxygen or air is directly used as an oxidizing agent. In page 762 of the "Lecture Draft II" (1994) of 67th Spring Annual Meeting of Chemical Society of Japan, it is reported that oxidation of an alcohol such as benzyl alcohol or benzhydrol with air using vanadomolybdophosphoriate and N-hydroxyphthalimide provides a ketone such as acetophenone or benzophenone in a high yield. Japanese Patent Application Laid-open No. 38909/1996 (JP-A-8-38909) discloses an oxidizing a substrate with oxygen by using the oxidation catalyst comprised an imide compound (e.g., N-hydroxyphthalimide) and a transition metal compound.

The catalytic systems show high activities in an oxidation of a substrate with oxygen. However, transformation rates or conversions or selectivities sometimes deteriorate depending on spieces of catalysts. When the catalytic activities are reduced and the amount of co-catalysts used is increased, it is difficult to continue the conduction of the oxidation reaction for a long time, because that the imide compound such as N-hydroxyphthalimide is deactivated in a short time.

SUMMARY OF THE INVENTION

It is, therefore, an object of the present invention to provide an oxidation catalytic system which is useful for enhancement of a catalytic activities and efficient oxidation of a substrate, an oxidation process using this catalytic system and a process for producing an oxide.

It is another object of the invention to provide an oxidation catalytic system that could maintain high activities with inhibiting a deactivation of imide compound, an oxidation process using this catalytic system and a process for producing an oxide.

A further object of the invention is to provide an oxidation catalytic system which is useful for producing an oxide (e.g., a ketone, an alcohol, an aldehyde, a carboxylic acid) with high transformation rates or conversions and selectivities, an oxidation process using this catalytic system and a process for producing an oxide.

The present inventors did much investigation to accomplish the above objects, and as a result, found that a complexed catalytic system constituted with a combination of plural transition metal compounds enhances the catalytic activities and selectivities and reveals stabilization effects depending on the spieces of catalysts, and the use of a co-catalyst with specific amount for the imide compound inhibits the deactivation of the imide compound and maintains the high activities. The present invention has been accomplished based on the above findings.

Thus, the oxidation catalytic system of the present invention comprises an imide compound shown by the following formula (I),

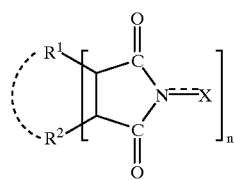

(1)

wherein R¹ and R² respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or R¹ and R² may bond together to form a double bond, or an aromatic or non-aromatic ring; X represents an oxygen atom or a hydroxyl group; n denotes an integer of 1 to 3, and a co-catalyst, the co-catalyst is composed of the plural transition metal compounds. Provided that in the case that a polyacid comprises Group 5 or 6 elements of the Periodic Table of Elements, the polyacid is an isopolycid. A catalytic system comprising a combination of Group 7 and 8 elements of the Periodic Table Elements is excluded.

In this oxidation catalytic system, a compound comprising the co-catalysts is (A) a single compound containing plural elements selected from different Groups or plural compounds containing an element selected from different Groups, or (B) a single compound containing transition metal elements having plural different valencies selected from the same Group or plural compounds containing a transition metal element having different valencies selected from the same Group.

A co-catalyst comprises, for example, an oxide, an organic acid salt, an inorganic acid salt, a halide, a complex, and an isopolyacid. Selecting the co-catalyst component and/or reducing a ratio of co-catalyst relative to an imide compound are advantageous to enhance the stability of the catalyst.

A process of the present invention also comprises a process for oxidizing a substrate by contacting the substrate with oxygen in the presence of the oxidataion catalytic system and a process for producing corresponding a ketone, an alcohol, an aldehyde, or a carboxylic acid by contacting the substrate with oxygen in the presence of the oxidataion catalytic system.

It should be understood that the term "carboxylic acid" as used in this specification means and includes not only compounds each having a free carboxyl group but also derivatives of carboxylic acids being substantially equivalent to the carboxylic acids, such as salts, esters or acid anhydrides which form according to reaction conditions. A "non aromatic cyclic compound" comprises a cyclic hydrocarbon (e.g., a cycloalkane and cycloalkene) and a heterocyclic compound, and may comprise, for example, a compound having a condenced ring to a aromatic ring, all compounds having a methylene chain in a ring are included. Above nonaromatic cyclic compounds may have an aromatic substituent.

The adamantane and its derivative may be simply called "the adamantane component." In the polycyclic hydrocarbon, the methylidyne group in a bridgehead position is shown by the group "—HC<," and the methylidyne group in a junction position (a fusing site) of adjacent rings may be shown by the group ">CH—CH<." The term "the divalent transition metal compound" includes transition metal compounds that have formed in the reaction system, as well.

DETAILED DESCRIPTION OF THE INVENTION

Imide Compound

In the compound shown by the formula (1), the halogen atom, as the substituents R¹ and R², includes iodine, bromine, chlorine and fluorine atoms. The alkyl group includes, for example, methyl, ethyl, propyl, isopropyl, butyl, isobutyl, sec-butyl, t-butyl, pentyl, hexyl, heptyl, octyl, decyl, or other straight chain or branched chain alkyl groups each having about 1 to 10 carbon atoms. An illustrative preferred alkyl group includes alkyl groups each having about 1 to 6 carbon atoms, in particular lower alkyl groups each having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups. The alkoxy group includes, for example, methoxy, ethoxy, propoxy, isopropoxy, butoxy, isobutoxy, t-butoxy, pentyloxy, hexyloxy, and other alkoxy groups each having about 1 to 10 carbon atoms. Among them, alkoxy groups each having about 1 to 6 carbon atoms, in particular lower alkoxy groups each having about 1 to 4 carbon atoms are desirable.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. A preferred alkoxycarbonyl group includes those each having about 1 to 6 carbon atoms in the alkoxy moiety, among which lower alkoxycarbonyl groups each having about 1 to 4 carbon atoms in the alkoxy moiety are typically desirable.

The acyl group includes, for instance, formyl, acetyl, propionyl, butyryl, isobutyryl, valeryl, isovaleryl, pivaloyl, and other acyl groups each having about 1 to 6 carbon atoms.

The substituents R¹ and R² may be either the same or different from each other. In the formula (1), R¹ and R² may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, but it may practically be a hydrocarbon ring. As such a ring, there may be mentioned, for instance, non-aromatic alicyclic rings (e.g., cyclohexane ring and other cycloalkane rings which may have a substituent, cyclohexene ring and other optionally substituted cycloalkene rings), non-aromatic bridged (cross-linked) rings (e.g., 5-norbornene ring and other optionally substituted bridged hydrocarbon rings), benzene ring, naphthalene ring and other optionally substituted aromatic rings. The ring may practically comprise an aromatic ring.

A preferred imide compound includes compounds shown by the following formula,

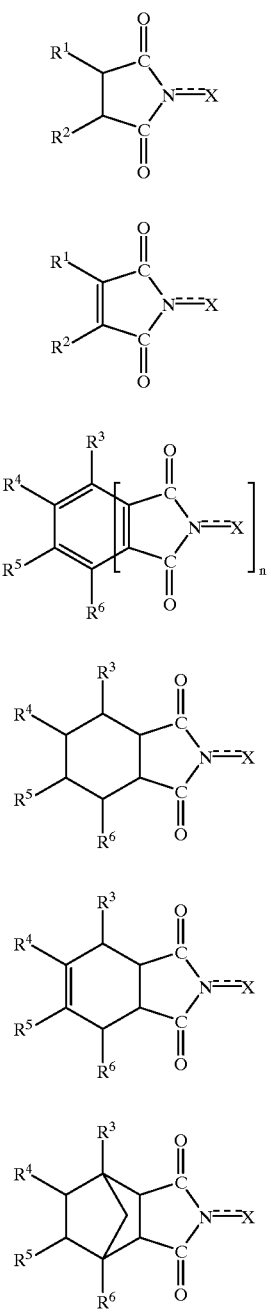

wherein $R^3$, $R^4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; the bond between the nitrogen atom "N" and "X" denotes a single bond or a double bond; and $R^1$, $R^2$, X and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular lower alkoxy groups each having about 1 to 4 carbon atoms. Examples of the alkoxycarbonyl group include the same alkoxycarbonyl groups as exemplified above, in especial lower alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol X in the formula (1) denotes an oxygen atom or a hydroxyl group. A bond between the nitrogen atom "N" and "X" is a single bond or a double bond. Further, n usually denotes about 1 to 3 and preferably 1 or 2. The imide compound shown by the formula (1) can be used singly or in combination in the oxidation reaction.

As examples of the acid anhydride corresponding to the imide compound of the formula (1), there may be mentioned succinic anhydride, maleic anhydride, or other saturated or unsaturated aliphatic dicarboxylic acid anhydrides, tetrahydrophthalic anhydride, hexahydrophthalic anhydride (1,2-cyclohexanedicarboxylic anhydride), 1,2,3,4-cyclohexanetetracarboxylic acid 1,2-anhydride, and other saturated or unsaturated nonaromatic cyclic polycarboxylic acid anhydrides (alicyclic polycarboxylic anhydrides), hetic anhydride, himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8:4,5-naphthalenetetracarboxylic dianhydride, and other aromatic polycarboxylic anhydrides.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide and so forth. A typically preferable imide compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

These imide compounds are combined with the co-catalyst comprising a plurality of transition metal compounds to express high activities. The catalytic system could oxidize efficiently a substrate with the oxygen or air even in mild or moderate conditions, and improves the conversion and/or the selectivity. Specifically, the catalytic system are useful for controling catalytic activities (e.g., elevation of activities and selectivities and stabilities). Therefore, according to the present invention, the substrate is oxidized efficiently in the presence of the oxidation catalytic system comprising the imide compound and the co-catalyst to give a corresponding ketone, alcohol, aldehyde or carboxylic acid. Accordingly, this invention provides efficient oxidation of the substrate with high selectivity in the presence of the catalytic system composed of the imide compound and the co-catalyst to form a ketone, alcohol, aldehyde or carboxylic acid corresponding to the substrate.

Co-Catalyst

A feature of the present invention resides in that the co-catalyst comprises plural transition metal compounds. As the elements of the transition metal, there may be mentioned, for instance, Group 3 elements of the Periodic Table of Elements (e.g., scandium Sc, yttrium Y, and lanthanum La, cerium Ce, samarium Sm and other lanthanoid elements, actinium Ac and other actinoid elements), Group 4 elements of the Periodic Table of Elements (e.g., titanium Ti, zirconium Zr, hafnium Hf), Group 5 elements (e.g., vanadium V, niobium Nb, tantalum Ta), Group 6 elements (e.g., chromium Cr, molybdenum Mo, tungsten W), Group 7 elements (e.g., manganese Mn, technetium Tc, rhenium Re), Group 8 elements (e.g., iron Fe, ruthenium Ru, osmium Os), Group 9 elements (e.g., cobalt Co, rhodium Rh, iridium Ir), Group 10 elements (e.g., nickel Ni, palladium Pd, platinum Pt), Group 11 elements (e.g., copper Cu, silver Ag, gold Au) and Group 12 elements of the Periodic Table of Elements (e.g., zinc Zn, cadmium Cd).

A preferred transition metal element constituting the co-catalyst includes, for example, Group 4 elements (e.g., Ti, Zr), Group 5 elements (e.g., V), Group 6 elements (e.g., Cr, Mo, W), Group 7 elements (e.g., Mn, Tc, Re), Group 8 elements (e.g., Fe, Ru), Group 9 elements (e.g., Co, Rh), Group 10 elements (e.g., Ni) and Group 11 elements (e.g., Cu) of the Periodic Table of Elements. As a prefered compound constituting the co-catalyst, a compound comprising a element selected from the group consisting from Ti, Zr, V, Cr, Mo, W, Mn, Fe, Ru, Co, Rh, Ni and Cu is employed.

The species of the co-catalyst is not particularly limited as far as it expresses an oxidation activity and may be a simple substance or hydroxide of a metal. The co-catalyst is usually a metal oxide (double oxide or oxygen acid salt), an organic acid salt, an inorganic acid salt, a halide, each of which contains the element, a coordinate compound (a complex), a polyacid (in particular, an isopolyacid) or its salt, each of which contains the metal element.

When the co-catalyst is a polyacid containing Group 5 and/or 6 elements, the co-catalyst is a isopolyacid, a heteropolyacid comprising Group 5 and 6 elements of the Periodic Table of Elements (vanadomolybdic acid which is heteropolyacid of vanadium-molybden series) is excluded. Further, a catalytic system comprising a combination of Group 7 and 8 elements of the Periodic Table of Elements is also excluded.

The hydroxide includes $Mn(OH)_2$, $MnO(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and so forth. As examples of the double oxide or oxygen acid salt, there may be mentioned $MnAl_2O_4$, $MnTiO_3$, $LaMnO_3$, $K_2Mn_2O_5$, $CaO.xMnO_2$ (x=0.5, 1, 2, 3, 5), manganese salts [e.g., $Na_3MnO_4$, $Ba_3[MnO_4]_2$ and other manganates(V), $K_2MnO_4$, $Na_2MnO_4$, $BaMnO_4$, and other manganates(VI), $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$, and other permanganates].

As the organic acid salts, there may be exemplified as cobalt acetate, manganese acetate, cobalt propionate, manganese propionate, cobalt naphthenate, manganese naphthenate, cobalt stearate, manganese stearate, and other salts with a $C_{2-20}$ fatty acid, manganese thiocyanate, and corresponding salts of Ce, Ti, Zr, V, Cr, Mo, Fe, Ru, Ni, Pd, Cu and Zn. The inorganic acid salt includes, for instance, cobalt nitrate, iron nitrate, manganese nitrate, nickel nitrate, copper nitrate, and other nitrates, and sulfates, phosphates and carbonates each corresponding to these nitrates (e.g., cobalt sulfate, iron sulfate, manganese sulfate, cobalt phosphate, iron phosphate, manganese phosphate, an Iron carbonate, a manganese carbonate, iron perchlorate). As the halides, there may be mentioned, for instance, $SmCl_3$, $SmI_2$, $TiCl_2$, $ZrCl_2$, $ZrOCl_2$, $VCl_3$, $VOCl_2$, $MnCl_2$, $MnCl_3$, $FeCl_2$, $FeCl_3$, $RuCl_3$, $CoCl_2$, $RhCl_2$, $RhCl_3$, $NiCl_2$, $PdCl_2$, $PtCl_2$, $CuCl$, $CuCl_2$, and other chlorides, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, $CuBr$, $CuBr_2$), and other halides, $M^1MnCl_3$, $M^1{}_2MnCl_4$, $M^1{}_2MnCl_5$, $M^1{}_2MnCl_6$, wherein $M^1$ represents a monovalent metal, and other complex halides.

The ligand of the complex includes, for example, OH (hydroxo), methoxy, ethoxy, propoxy, butoxy and other alkoxy groups, acetyl, propionyl and other acyl groups, methoxycarbonyl (acetato), ethoxycarbonyl and other alkoxycarbonyl groups, acetylacetonato, cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$ (nitro), $NO_3$ (nitrato), ethylenediamine, di-ethylenetriamine, pyridine, phenanthroline and other nitrogen-containing compounds. In the complexes or complex salts, the same or different ligands may be coordinated singly or in combination.

The ligand is practically, for example, OH, an alkoxy group, an acyl group, an alkoxycarbonyl group, acetylacetonato, a halogen atom, CO, CN, $H_2O$ (aquo), triphenylphosphine or other phosphorus compounds, or a nitrogen-containing compound inclusive of $NH_3$, $NO_2$ and $NO_3$.

The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], cyano complexes [e.g., hexacyanomanganate(I), hexacyanoferrate (II)], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$]

The polyacid is polyacid (isopolyacid and heteropolyacid) excepting for heteropolyacid comprising Group $_5$ and $_6$ elements of the Periodic Table of Elements, such as V (vanadic acid), Mo (molybdic acid) or W (tungstic acid), typically speaking. There is no particular limit as to the central atom, and it may be any of, for instance, Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, Pt, or Cu. As illustrative examples of the polyacid, there may be mentioned isopolyacid (e.g., vanadic acid, molybdic acid, tungstic acid), heteropolyacid (e.g., cobaltmolybdate, cobalttungstate, molybdenumtungstate, manganesemolybdate, manganesetungstate, manganesemolybdenumtungstate, manganesevanadiummolybdate, and manganesevanadomolybdophosphate). As above described, in the co-catalyst of the oxidation catalytic system of the present invention, a preferred polyacid is an isopolyacid.

A co-catalyst comprises (A) a single compound comprising plural elements selected from different Groups or plural compounds comprising a element selected from different Groups, or (B) a single compound comprising transition metal elements having plural different valencies selected from the same Group or plural compounds comprising a transition metal element having different valencies selected from the same Group. The co-catalysts of (A) and (B) may be employed in combination. Practically, (A) and (B) may be together cosntituted with plural compounds, and are constituted in suitable combination of elements of Group 3 to 12 of the Priodic Table of Elements or compounds thereof.

(A) A co-catalyst cmprising plural elements selected from different Groups

In the case that the co-catalyst comprises plural elements selected from different Groups, the combination of prefered plural elements or compounds are, for instance, as follows.

(a) a combination of Group 3 elements (e.g., Ce, Sm) of the Priodic Table of Elements or compounds thereof and at least one element or compound thereof selected from Group 4 elements (e.g., Ti, Zr), Group 5 elements (e.g., V), Group 6 elements (e.g., Cr, Mo), Group 7 elements (e.g., Mn), Group 8 elements (e.g., Fe, Ru), Group 9 elements (e.g., Co), Group 10 elements (e.g., Ni), Group 11 elements (e.g., Cu), and Group 12 elements (e.g., Zn) of the Priodic Table of Elements (b) a combination of Group 4 elements of the Piriodic Table of Elements or compounds thereof and at least one element or compound thereof selected from Group 5 elements, Group 6 elements, Group 7 elements Group 8 elements, Group 9 elements, Group 10 elements, Group 11 elements, and Group 12 elements of the Priodic Table of Elements (c) a combination of Group 5 elements of the Piriodic Table of Elements or compounds thereof and at least one element or compound thereof selected from Group 6 elements, Group 7 elements, Group 8 elements, Group 9 elements, Group 10 elements, Group 11 elements, and Group 12 elements of the Priodic Table of Elements (d) a combination of Group 6 elements of the Piriodic Table of Elements or compounds thereof and at least one element or compound thereof selected from Group 7 elements, Group 8 elements, Group 9 elements, Group 10 elements, Group 11 elements, and Group 12 elements of the Priodic Table of Elements (e) a combination of Group 7 elements of the Piriodic Table of Elements or compounds thereof and at least one element or compound thereof selected from Group 9 elements, Group 10 elements, Group 11 elements, and Group 12 elements of the Priodic Table of Elements (f) a combination of Group 8 elements of the Piriodic Table of Elements or compounds thereof and at least one element or compound thereof selected from Group 9 elements, Group 10 elements, Group 11 elements, and Group 12 elements of the Priodic Table of Elements (g) a combination of Group 9 elements of the Piriodic Table of Elements or compounds thereof and at least one element or compound thereof selected from Group 10 elements, Group 11 elements, and Group 12 elements of the Priodic Table of Elements (h) a combination of Group 10 elements of the Piriodic Table of Elements or compounds thereof and at least one element or compound thereof selected from Group 11 elements, and Group 12 elements of the Priodic Table of Elements (i) a combination of Group 11 elements of the Piriodic Table of Elements or compounds thereof and at least one element of Group 12 elements of the Priodic able of Elements or compound thereof Prefered combination of elements or compounds includes the combinations (b) to (h), particularly the combinations (c) to (g).

More prefered combination of elements or compounds is as follows.

(c1) a combination of Group 5 elements (e.g., V) of the Priodic Table of Elements or compounds thereof and at least one element selected from Group 6 elements, Group 7 elements, Group 8 elements, Group 9 elements, Group 10 elements, and Group 11 elements of the Priodic Table of Elements or compounds thereof (e1) a combination of Group 7 elements (e.g., Mn) of the Priodic Table of Elements or compounds thereof and at least one element selected from Group 9 elements, Group 10 elements, and Group 11 elements of the Priodic Table of Elements or compounds thereof (f1) a combination of Group 8 elements (e.g., Fe) of the Priodic Table of Elements or compounds thereof and at least one element selected from Group 9 elements, Group 10 elements, and Group 11 elements of the Priodic Table of Elements or compounds thereof (g1) a combination of Group 9 elements (e.g., Co) of the Priodic Table of Elements or compounds thereof and at least one element selected from Group 10 elements and Group 11 elements of the Priodic Table of Elements or compounds thereof Further the co-catalyst may comprise Group 1 elements (e.g., potassium, sodium, lithium), Group 2 elements (e.g., Magnesium, Carsium, Strontium, Barium), Group 13 elements (e.g., Boron B, Alminium Al) of the Priodic Table of Elements. A co-catalyst, for instance, may comprise a compound containing Group 2 elements of the Priodic Table of Elements, or may comprise a boron compound. As the boron compound, there may be mentioned, for example, a boron hydride (e.g., borane, diborane, tetraborane, pentaborane, decaborane), a boric acid (e.g., orthoboric acid, metaboric acid, tetraboric acid), a borate (e.g., a nickel borate, magnesium borate, manganese borate), $B_2O_3$, and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate) and so on. A preferred boron compound includes boron hydrides, orthoboric acid, and other boric acids or salts thereof, among which a boric acid can preferably be employed.

Depending on the species of the elements constituting the co-catalyst, any of the following characteristic functions, for example, can be exhibited.

1. In the constitutive transition metal compound of the co-catalyst, the valency of the element is not particularly restricted, and it may be about from two to six valencies. Use of a divalent transition metal compound (e.g., Group 8 elements of the Priodic Table of Elements such as a divalent cobalt compound, Group 7 elements of the Priodic Table of Elements such as a divalent manganese compound) as the co-catalyst enhances oxidation activity. By way of illustration, a catalytic system using a divalent transition metal compound as a co-catalyst in lieu of a trivalent transition metal compound induces an oxidized product in a short time with high selectivity and yield. Further, when the divalent transition metal compound is used as the co-catalyst, the substrate (e.g., an aromatic compound substituted with a methyl group) can be oxidized quantitatively to form a corresponding oxide (e.g., a carboxylic acid) even at a low temperature (e.g., 10 to 60° C.), in particular at room temperature (about 15 to 30° C.).

2. Use of a compound containing at least one element selected from Group 4 elements (e.g., Ti, Zr), Group 6 elements (e.g., Cr, Mo) and Group 7 elements (e.g., Mn) of the Periodic Table of Elements as the co-catalyst component inhibits inactivation (deactivation) of the imide compound and stabilizes the catalitic system even in severe reaction conditions.

3. The use of a compound containing the Group 4 element (e.g., Ti, Zr), Group 5 element (e.g., V), Group 6 element (e.g., Cr, Mo), Group 7 element (e.g., Mn) Group 8 element (e.g., Fe), and Group 9 element (e.g., Co) of the Periodic Table of Elements as the co-catalyst component results in remarkable enhancement of the oxidizing activity and provides effective oxidation of the substrate. By way of an example, a catalytic system comprising, as the co-catalyst component, a compound containing the Group 5 element (e.g., V), Group 7 element (e.g., Mn) or Group 9 element (e.g., Co) of the Periodic Table of Elements has high activities. In particular, when a compound containing the Group 5 element (e.g., V) is used as the co-catalyst component, plural positions or sites of the substrate [e.g., a bridgehead position or junction position of the polycyclic hydrocarbon (e.g., adamantane)] can be efficiently oxidized to give a product having plural hydroxyl groups (e.g., an adamantanepolyol).

4. The use of the co-catalyst containing the Group 11 element of the Periodic Table of Elements (e.g., Cu) as the oxidation catalytic system insures great improvement of the selectivity in the oxidation reaction, and inhibits deactivation of the imide compound. Therefore, this use is advantageous for commercial production.

5. A use of the co-catalyst containing Group 9 elements and Group 5 or 6 elements of the Priodic Table of Elements inhibits generation of a dicarboxylic acid and provides a ketone or an alcohol in high electivities. In this case, a combination use of rivalent elements and di or pentavalent elements has great effect.

(B) a co-catalyst comprising plural elements having different valencies selected from the same group.

In the case that a co-catalyst comprises plural elements having different valencies selected from the same group, the plural elements may be whichever the same or different element as far as the elements belong to the same group and has different valencies. Prefered elements are Group 4 to 11, particularly Group 9 elements of the Priodic Table of Elements (e.g., Co, Rh). A combination of the elements comprising a co-catalyst may be a suitable combination selected from monovalent to hexavalent elements of the Priodic Table of Elements, the combination selected from divalent to tetravalent elements of the Priodic Table of Elements (e.g., a combination of divalent and trivalent elements of the Priodic Table of Elements) is preferably. The use of the present co-catalyst not only enhances the ability of oxidation but also inhibits the generation of dicarboxylic acid and provides a ketone or an alcohol efficiently in the case of using non-aromatic cyclic compounds such as a cycloalkane as a substrate.

In said co-catalyst comprising plural elements or compounds, the ratio of each elements or compounds is not strictly restricted, and can be seleted from the wide range such as the range of about 0.1 to 99.9 mole %, preferably about 1 to 99 mole %, in paticular about 5 to 95 mole % for whole co-catalysts (100 mole %). By way of illustration, in the case that the co-catalyst is constituted from the main first co-catalyst and the other co-catalyst, the ratio of the other co-catalyst relative to one mole of the main first co-catalyst is, for instance, about 0.01 to 5 mole (e.g., 0.01 to 2.5 mole), preferably about 0.02 to 1 mole, more preferably about 0.03 to 0.8 mole, respectively.

The oxidation catalyst may be whichever of a homogeneous system or a heterogeneous system. The oxidation catalyst system may be a solid catalyst comprising a catalytic component supported on a support or carrier, as well. As the support, use can be practically made of activated carbon, zeolite, silica, silica-alumina, bentonite, or other porous supports. In the solid catalyst, a supporting amount of the catalytic component may be such that a relative ratio of the imide compound of the formula (1) to 100 parts by weight of the support is about 0.1 to 50 parts by weight, preferably about 0.5 to 30 parts by weight and more preferably about 1 to 20 parts by weight. A ratio of the co-catalyst supported on the support is about 0.1 to 30 parts by weight, preferably about 0.5 to 25 parts by weight, and more preferably about 1 to 20 parts by weight, relative to 100 parts by weight of the support.

A relative ratio of the co-catalyst to the imide compound of the formula (1) may be selected from a range not interfering with the reaction rate and selectivity, and is, for example, about 0.001 to 10 moles, preferably about 0.005 to 5 moles, and more preferably about 0.01 to 3 moles relative to one mole of the imide compound. The co-catalyst may practically be employed in an amount of 0.01 to 5 moles (in particular 0.001 to 1 mole) relative to one mole of the imide compound.

Incidentally, the activity of the imide compound may sometimes deteriorate and can not sometimes maintains the high oxidation activities for long time with increasing the proportion of the co-catalyst. Therefore, for retaining the high activities of the oxidation catalytic system, a favorable ratio of the whole co-catalyst, relative to one mole of the imide compound, is not less than an effective amount and not greater than 10 mole % (e.g., about 0.1 to 10 mole %, preferably about 0.5 to 8 mole %, and more preferably about 1 to 7 mole %). The favorable oxdation catalytic systems may comprise usually the imide compound and the co-catalyst of about 1 to 8 mole % relative to the imide compound.

A proportion of the imide compound of the formula (1) in the oxidation reaction (i.e., in the production of a ketone, an alcohol, an aldehyde or an alcohol) is selected from a broad range of about 0.001 to 1 mole (0.01 to 100 mole %), preferably about 0.001 to 0.5 mole (0.1 to 50 mole %), more preferably about 0.01 to 0.30 mole and practically about 0.01 to 0.25 mole, on 1 mole of the substrate, typically speaking.

A proportion of the co-catalyst (a co-oxidizing agent) used in such a reaction, depending on the amount of the imide compound, can be liberally selected from a range not interfering with the activity and selectivity, and is, for example, about 0.0001 mole (0.1 mole %) to 0.7 mole (70 mole %), preferably about 0.0001 to 0.5 mole, and more preferably about 0.001 to 0.3 mole relative to one mole of the substrate. The co-catalyst is practically used in a ratio of 0.0005 to 0.1 mole (e.g., about 0.005 to 0.1 mole) per one mole of the substrate.

Substrate

The use of the oxidation catalyst comprising the imide compound and the co-catalyst comprising plural elements selected from different groups [herein after refers to oxidation catalytic system (A)], or the imide compound and the co-catalyst comprising a element having plural different valencies selected from the same group [herein after refers to oxidation catalytic system (B)] insures effective oxidation of various substrates with high conversion and selectivity, and provides ketones, alcohols, aldehydes or carboxylic acids each corresponding to the substrates. Incidentally, in the case of employing a non-aromatic cyclic compound as a substrate, the use of oxidation catalytic system (B) inhibits the generation of dicarboxylic acid etc. and provides selectively a compound in which a hydroxyl group or an oxo group is introduced at a methylene group.

A species of the substrate is not strictly limited, and saturated or unsaturated compounds in broad range can be employed. The substrate includes, for example, hydrocarbons (aliphatic hydrocarbons, alicyclic hydrocarbons, aromatic hydrocarbons), heterocyclic compounds, alcohols, ethers, esters, ketones, aldehydes and amines.

These substrates may have, according to the species of the substrate, any of various substituents. Examples of such substituents include halogen atoms (iodine, bromine, chlorine and fluorine atoms), alkyl groups (e.g., methyl, ethyl, propyl, isopropyl, butyl, isobutyl, sec-butyl, t-butyl, hexyl and other straight chain or branched chain alkyl groups each having about 1 to 6 carbon atoms, in particular lower alkyl groups each having about 1 to 4 carbon atoms), an oxo group, a hydroxyl group, alkoxy groups (e.g., methoxy, ethoxy, propoxy, isopropoxy, butoxy, isobutoxy, t-butoxy, hexyloxy and other alkoxy groups each having about 1 to 6 carbon atoms, in particular lower alkoxy groups each having about 1 to 4 carbon atoms), hydroxyalkyl groups (e.g., hydroxymethyl, 2-hydroxyethyl and other hydroxy-$C_{1-4}$ alkyl groups), a carboxyl group, alkoxycarbonyl groups (e.g., methoxycarbonyl, ethoxycarbonyl, propoxycarbonyl, isopropoxycarbonyl, butoxycarbonyl, isobutoxycarbonyl, t-butoxycarbonyl, hexyloxycarbonyl and other alkoxycarbonyl groups each having about 1 to 6 carbon atoms in the alkoxy moiety, in particular lower alkoxycarbonyl groups each having about 1 to 4 carbon atoms in the alkoxy moiety), acyl groups (e.g., formyl, acetyl, propionyl, butyryl, isobutyryl, valeryl, isovaleryl, pivaloyl, and other acyl groups each having about 1 to 6 carbon atoms), an amino group, a substituted amino group, a cyano group, a nitro group and the like.

As preferred substrates, there may be mentioned the following compounds that are useful for commercial applications.

(a) Cycloalkane

The cycloalkane includes, for instance, compounds each having a cycloalkane ring of 3 to 30 members, such as cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane, cyclotetracosane, or cyclotriacontane.

As the cycloalkanes having a substituent, there may be mentioned, for example, cycloalkanes each having a hydroxyl group (e.g., cyclohexanol, cyclooctanol, cyclodecanol, cycloundecanol, cyclododecanol, cyclotetradecanol, cycloicosanol), cycloalkanes each having an oxo group (e.g., cyclopentanone, cyclohexanone, methylcyclohexanone, dimethylcyclohexanone, cyclohexadione, cyclopentanone, cyclooctanone, cyclooctadione, cyclononanone, cyclodecanone, cycloundecanone, cyclododecanone, cyclotetradecanone, cyclooctadecanone, cycloicosanone), cycloalkanes each having an alkyl group (e.g., methylcyclohexane, 1,2-dimethylcyclohexane, isopropylcyclohexane, methylcyclooctane) and so on.

A preferred cycloalkane includes compounds each having a ring of about 5 to 30 members, in particular a ring of about 6 to 25 members, among which compounds each having a ring of about 6 to 20 members (e.g., a 6- to 16-membered ring) are desirable, typically speaking.

Further, according to the process of the present invention, effective oxidation can be achieved for compounds each having a ring of 8 members or more (e.g., a ring of about 8 to 30 members), preferably a ring of about 8 to 25 members, in particular, a ring of about 8 to 20 members (e.g., a ring of 8 to 16 members) which are commercially useful.

Oxidation of such a cycloalkane with oxygen in the presence of the oxidation catalytic system (A) mainly provides a corresponding dicarboxylic acid or cycloalkanone with a high conversion and selectivity even in air or oxygen atmosphere at ambient pressure (atmospheric pressure), and the presence of the oxidation catalytic system (B) provides a cycloalkanone or a cycloalkanol, selectively with inhibiting the generation of a dicarboxylic acid. By way of illustration, when cyclohexane is oxidized, adipic acid can efficiently be formed with high transformation rate and excellent selectivitiy by using the oxidation catalytic system (A), and cyclohexanone or cyclohexanol can be formed with high transformation rate and excellent selectivity by using the oxdation catalytic system (B). Incidentally, in the case that the co-catalyst contains di- or trivalent Group 9 elements of the Priodic Table of Elements and tri-, tetra- or pentavalent Group 5 or 6 elements of the Piriodic Table of Elements together, the oxidation of a cycloalkane produces a cycloalkanone or a cycloalkanol even in the presence of the oxidation catalytic system (A).

In the oxdation catalytic system (A), even a macrocyclic cycloalkane having 8 members or more, in particular 9 members or more (e.g., a 10- to 30-membered cycloalkane) can be oxidized efficiently to give a ketone (in particular, a monoketone) or a dicarboxylic acid in a high yield. Therefore, this process is remarkably useful for the production of a long-chain dicarboxylic acid having 8 or more carbon atoms, which is used as a raw material for polyester, polyamide or a plasticizer, or for the production of a monoketone compound that is a precursor of the long-chain dicarboxylic acid.

When the cycloalkane is used as the substrate, a practically effective co-catalyst comprising the oxidation catalytic system (A) is a binary system co-catalyst containing at least a Group 7 element (e.g., Mn) and a Group 9 element (e.g., Co) of the Periodic Table of Elements, even a polynary system catalyst containg a Group 8 element (e.g., Fe) or a Group 11 element (e.g., Cu) in addition to the elements shows high activities.

(b) Cycloalkene

Examples of the cycloalkene include compounds each having a cycloalkene ring having 3 to 30 members, such as a cyclic olefin (e.g., cyclopropene, cyclobutene, cyclopentene, cyclohexene, 1-methyl-1-cyclohexene, isophorone, cycloheptene, cyclooctene, cyclononene, cyclodecene, cyclodecaene, cyclododecaene), a cycloalkadiene (e.g., cyclopentadiene, 1,3-cyclohexadiene, 1,4- cyclohexadiene and other cyclohexadienes, 1,3-cycloheptadiene and other cycloheptadienes, 1,5-cyclooctadiene and other cyclooctadienes, cyclodecadiene, cyclododecadiene), a cycloalkatriene (e.g., cyclooctatriene), a cycloalkatetraene (e.g., cyclooctatetraene), and so forth. A preferred cycloalkene includes compounds each having a 3- to 30-membered ring (e.g., a 3- to 20-membered ring), preferably a 3- to 16-membered ring, and specifically a 3- to 12-membered ring (e.g., a 5- to 10-membered ring).

As illustrative cycloalkenes having a substituent, there may be mentioned a cycloalkene having a $C_{1-4}$ alkyl group, a hydroxyl group, a hydroxyalkyl group, or a carboxyl group (e.g., cyclohexenecarboxylic acid, cyclohexenedicarboxylic acid, cyclohexadienecarboxylic acid, cyclohexadienedicarboxylic acid, cyclogeranic acid, cyclogeraniol, cyclocitral, cyclogeraniolene), and a cycloalkenone having an oxo group (e.g., cyclohexenone, cyclooctenone).

The oxdation of a cycloalkene with oxygen by using the oxdation catalytic system (A) or (B) provides a corresponding oxide of the cycloalkene (e.g., a ketone, an alcohol, an aldehyde or a carboxylic acid), in particular, a cycloalkenone or a cycloalkenol with high selectivity.

(c) Polycyclic hydrocarbon having a methylidyne group as a constitutive element of the ring The polycyclic hydrocarbon includes bridged cyclic hydrocarbons (e.g., cross-linked hydrocarbons, terpenes) and condensed polycyclic hydrocarbons each having at least one methylidyne group (i.e., methine carbon-hydrogen bond —CH<). The ring having the methylidyne group is usually a non-aromatic ring, and it may be a bridged ring or a condensed ring each having an unsaturated double bond. A condensed polycyclic hydrocarbon that has been ortho-condensed or ortho and peri-condensed may have an aromatic ring condensed thereto as far as having a non-aromatic ring containing a methylidyne group. In such a polycyclic hydrocarbon, two or more methylidyne groups are practically present in the bridgehead positions and/or junction positions (fusing sites).

Some bridged cyclic hydrocarbons may form condensed polycyclic hydrocarbons in which adjacent rings bond each other in or at two common methylidyne groups. In such a compound, it is possible to oxidize at least one methylidyne group in the bridgehead position and junction position and introduce a hydroxyl group into a tertiary carbon atom. A position of the hydroxyl group to be introduced may be selected according to the species of the substrate. The oxo group may practically be introduced into an adjacent position (a secondary carbon atom) to the bridgehead position or junction position.

As the cross-linked cyclic hydrocarbon among the bridged cyclic hydrocarbons, there may be mentioned, for example, bicyclic hydrocarbons (e.g., thujane, carane, pinane, bornane (camphane), bornylene, norbornene, norbornane, bicyclo[3.2.1]octane, bicyclo[4.3.2]undecane), tricyclic hydrocarbons (e.g., tricyclo[4.3.1.1$^{2,5}$]undecane, homobrendane (i.e., tricyclo[5.2.1.0$^{3,8}$]decane), adamantane, exotricyclo[5.2.1.0$^{2,6}$]decane, endotricyclo[5.2.1.0$^{2,6}$]decane, tricyclo[4.3.1.1$^{2,5}$]undecane, endotricyclo[5.2.2.0$^{2,6}$]undecane), tetracyclic hydrocarbons (e.g., tetracyclo[4.4.0.1$^{2,5}$.1$^{7,10}$]dodecane), and dicyclohexadiene, dicyclopentadiene and other dimers of dienes, hydrogenated products of these dimers (e.g., dicyclohexane, dicyclohexene, dicyclopentane, dicyclopentene) and their derivatives.

As the cross-linked cyclic hydrocarbons, use may be practically made of bicyclic through tetracyclic hydrocarbons each having about 7 to 16 constitutive carbon atoms of the rings (in particular, about 6 to 14 constitutive carbon atoms of the rings), inclusive of compounds each having carbon-hydrogen bonds in 2 or more bridgehead positions or junction sites. Among them, pinane, bornane, bornylene, norbornene, norbornane and other bicyclic hydrocarbons, tricyclo[4.3.1.1$^{2,5}$]-undecane, homobrendane, adamantane and other tricyclic hydrocarbons may advantageously be employed. The cross-linked cyclic hydrocarbon in which a hydroxyl group can be introduced into a tertiary carbon atom in or at a bridgehead position includes, for instance, norbornene, tricyclo[4.3.1.1$^{2,5}$]undecane, homobrendane, adamantane and derivatives of these compounds.

Examples of the cross-linked cyclic hydrocarbon, in which a hydroxyl group can be introduced into a tertiary carbon atom in or at a junction site, include exotricyclo[5.2.1.0$^{2,6}$]decane, endotricyclo[5.2.1.0$^{2,6}$]-decane, tricyclo[4.3.1.1$^{2,5}$]undecane, endotricyclo-[5.2.2.0$^{2,6}$]undecane, tetracyclo[4.4.0.1$^{2,5}$.1$^{7,10}$]-dodecane, and the like.

As the terpenes, there may be mentioned, for instance, monocyclic monoterpenes (e.g., limonene, terpinolene, terpinene, phellandrene, menthene), bicyclic monoterpenes (e.g., carone, pinene, pinane, camphor, camphene, bornene, thujone, phencone), monocyclic sesquiterpenes (e.g., bisabolene, zingiberene), bicyclic sesquiterpenes (e.g., cadinene, santalene, selinene, santonin, caryophyllene), tricyclic sesquiterpenes (e.g., copaene, santalene, longifolene), diterpenes (e.g., vitamin A), triterpenes (e.g., ambrein, amyrin, lupeol), tetraterpenes (e.g., carotene, lutein and other carotenoids), polyterpenes and derivatives of these compounds.

The condensed polycyclic hydrocarbon includes various compounds formed by hydrogenation of condensed polycyclic aromatic hydrocarbons each condensed with a 5- to 8-membered ring, typically speaking. Such a compound includes, for instance, decalin, perhydroacenaphthylene, perhydroanthracene, perhydrophenanthrene, perhydrophenalene, hexahydroindane and so on. In the condensed polycyclic hydrocarbon, a five- or six-membered ring may practically be condensed, and the methylidyne group in or at a junction site may usually be oxidized.

As examples of the derivative of the cross-linked cyclic hydrocarbon among the polycyclic hydrocarbons each having a substituent, there may be mentioned a derivative having a halogen atom (e.g., 2-chloronorbornane, 1-chloroadamantane, 1,3-dichloroadamantane), a derivative having an alkyl group (e.g., 2,2-dimethylnorbornane, 2,7,7-trimethyl-2-norbornene, 1-methyladamantane, 1-ethyladamantane, 1-n-propyladamantane, 1-isopropyladamantane, 1-n-butyladamantane, 1-s-butyladamantane, 1-t-butyladamantane, 1-pentyladamantane, 1-hexyladamantane, 1-cyclohexyladamantane, 1,3-dimethyladamantane, 1-methyl-3-ethyladamantane, 1,3-dicyclohexyladamantane, 1,3,5-trimethyladamantane, 1-ethyl-3,5-dimethyladamantane, hemiadamantane, and other compounds each having an alkyl group containing about 1 to 6 carbon atoms), a derivative having a hydroxyl group (e.g., camphenilol, borneol, isoborneol, 1-adamantanol, 1,3-adamantanediol, 1,3,5-adamantanetriol, 1-methyl-3-adamantanol, 1-methyl-3,5-adamantanediol, 1-ethyl-3-adamantanol, 1-ethyl-3,5-adamantanediol, 1,3-dimethyl-5-adamantanol, 1-methyl-3-ethyl-5-adamantanol, 1-propyl-3-adamantanol, 1-propyl-3,5-adamantanediol), a derivative having an alkoxy group (e.g., 1-methoxyadamantane, 1,3-dimethoxyadamantane, 1-ethoxyadamantane, 1,3-diethoxyadamantane), a derivative having an oxo group (e.g., camphorquinone, camphenilone, 2-adamantanone, methyladamantanone, dimethyladamantanone), a derivative having an acyl group (e.g., formylnorbornene, formyladamantane), a derivative having a carboxyl group (e.g., camphanic acid, camphenylic acid), a derivative having an alkyloxycarbonyl group (e.g., methoxycarbonylcamphane, ethoxycarbonylcamphenyl), a derivative having an amino group (e.g., bornylamine), a derivative having a vinyl group (e.g., vinylnorbornene), and so forth.

As the cyclic terpene derivatives, there may be mentioned, for example, cyclic terpene alcohols (e.g., menthol, carbomenthol, terpineol, terpineol, carveol), cyclic terpene aldehydes (e.g., menthone, carbomenthone, phellandral, perillaldehyde), cyclic terpene ketones (e.g., ionone, irone, menthone, carbomenthone, thujone), cyclic terpene oxides (e.g., cineol, pinol, ascaridol), cyclic terpene carboxylic acids (e.g., camphenic acid, camphoric acid, abietic acid, neoabietic acid, levopimaric acid, dextropimaric acid), and so on.

The derivatives of the condensed polycyclic hydrocarbon includes a derivative having an alkyl group (e.g., methyldecalin, ethyldecalin, n-propyldecalin, isopropyldecalin, n-butyldecalin, s-butyldecalin, t-butyldecalin, cyclohexyldecalin, dimethyldecalin, methylethyldecalin, trimethyldecalin, ethyldimethyldecalin, tetramethyldecalin, and hexahydroindanes corresponding to these compounds), a derivative having a hydroxyl group (e.g., decalol), a derivative having an oxo group (e.g., decalone), a derivative having a carboxylic acid (e.g., decalincarboxylic acid), and a derivative having an amino group (e.g., decalylamine), typically speaking.

The use of the oxidation catalytic system (A) or (B) insures efficient oxidation, with oxygen, of the polycyclic hydrocarbon containing a methylidyne group as a constitutive unit of the ring, and provides an oxide (a ketone, an alcohol, an aldehyde, a carboxylic acid) of the polycyclic hydrocarbon, in particular a ketone or an alcohol thereof with high selectivity. Specifically, the process of the present invention, in which the polycyclic hydrocarbon (e.g., a polycyclic hydrocarbon having 2 to 4 rings containing methylidyne groups in a plurality of bridgehead positions or junction sites) is allowed to contact oxygen, provides a hydroxyl group-containing polycyclic hydrocarbon having a hydroxyl group being introduced into the bridgehead position or junction site with high selectivity and an excellent yield.

To be specific, the use of (1) a catalytic system which employs the divalent transition metal compound as a co-catalyst or (2) a catalytic system which employs the compound containing an element selected from Group 4 elements (e.g., Ti, Zr), Group 5 elements (e.g., V), Group 6 elements (e.g., Cr, Mo), Group 7 elements (e.g., Mn) or Group 9 elements (e.g., Co) of the Periodic Table of Elements insures improvement of the conversion of the polycyclic hydrocarbon, and it provides a hydroxyl group-containing polycyclic hydrocarbon with high selectivity and an enhanced yield.

When the adamantane component is used as the substrate, an adamantanepolyol may be formed by introducing hydroxyl groups into plural bridgehead positions of adamantane directly or indirectly, according to the process of the invention. Such an adamantanepolyol having hydroxyl groups introduced into plural bridgehead positions may be prepared by any of the following technologies: (1) a process of contacting the adamantane component selected from adamantane or its derivative with oxygen in the presence of the oxidation catalytic system (A) or (B), or (2) a process of contacting the adamantane component containing at least one component selected from an adamantanemonool and an adamantanediol in the presence of the oxidation catalytic system (A) or (B) to give an adamantanepolyol which has been further hydroxylated. When the adamantanepolyol is prepared according to the process (2), the adamantane component may only be subjected to the reaction in the coexistence of at least an alcohol of adamantane. The ratio of the adamantanemonool or adamantanediol is not strictly limited, and is about 5 mole % or more (e.g., about 10 to 100 mole %), preferably about 20 to 100 mole % and more preferably about 30 to 100 mole %, based on the total amount of the adamantane component.

According to these processes, depending on the kinds of the catalytic system, an effective inhabitation of the formation of a ketone that becomes significant disturbance to isolation and purification of the adamantanepolyol can be realized, and provides an adamantanepolyol in a remarkably improved yield. By way of example, when the adamantane component is oxidized by employing a divalent transition metal compound (e.g., a divalent cobalt compound) as at least one component of the co-catalyst, a polyol such as an adamantanediol can be obtained with high selectivity and an enhanced yield even in mild or moderate conditions. In such preparation, a ketone is scarcely by-produced.

Further, the use of a compound, as a component of the co-catalyst, containing an element selected from Group 4 elements, Group 5 elements, Group 6 elements, Group 7 elements, Group 8 elements and Group 9 elements of the Periodic Table of Elements insures production of a polyol such as an adamantanediol, in particular an adamantanetriol or adamantanetetraol from the adamantane component with improved selectivity and an excellent yield even in mild or moderate conditions. Practically, the co-catalyst may comprise a plurality of compouds containing an element selected from Group 5 elements, Group 6 elements, Group 7 elements, Group 8 elements and Group 9 elements of the Periodic Table of Elements. Among them, the use of a compound containing at least the Group 5A element (e.g., V) as one component of the co-catalyst provides an adamantanetetraol from the adamanatane component with high seletivity and yield, directly.

(d) Aromatic compound having a methyl group or methylene group in an adjacent position of an aromatic ring The aromatic compound may only be an aromatic compound having at least one methyl group or methylene group being substituted on the aromatic ring. The aromatic ring may be whichever of an aromatic hydrocarbon ring or an aromatic heterocyclic ring. When the aromatic compound is a ring-assembled compound in which aromatic rings bond each other, such as biphenyl, terphenyl, binaphthalene or bipyridine, at least one aromatic ring may be substituted with a methyl group or methylene group. The methyl group or methylene group in the aromatic heterocyclic ring may be bonded to the heterocyclic ring or to an hydrocarbon ring. A preferred compound includes a compound having a methyl group or methylene group at the benzyl position.

As examples of the aromatic hydrocarbon ring, there may be mentioned a benzene ring, condensed cyclic hydrocarbon rings (e.g., naphthalene, anthracene, phenanthrene, triphenylene, pyrene, chrysene, naphthacene, benzanthracene, and other condensed rings having an ortho-condensation or ortho and peri-condensation form of 2 to 8 benzene rings).

Examples of the aromatic heterocyclic ring include a heterocyclic ring having an oxygen atom as a hetero-atom (e.g., furan, oxazole, isooxazole and other 5-membered rings, pyran and other 6-membered rings, benzofuran, isobenzofuran, dibenzofuran, xanthone, xanthene, chroman, isochroman, chromene and other condensed rings), a heterocyclic ring containing a sulfur atom as a hetero-atom (e.g., thiophene, thiazole, isothiazole, thiadiazole, benzothiophene), a heterocyclic ring containing a nitrogen atom as a hetero-atom (e.g., pyrrole, pyrazole, imidazole, triazole and other 5-membered rings, pyridine, pyridazine, pyrimidine, pyrazine and other 6-membered rings, indole, indolene, isoindole, indazole, indoline, isoindoline, quinoline, isoquinoline, quinolinequinoline, quinoxaline, quinazoline, phthalazine, purine, carbazole, acridine, naphthoquinoline, phenanthrodine, phenanthroline, naphthyridine, benzoquinoline, phenoxazine, phthalocyanine, anthracyanine and other condensed rings), and the like.

The aromatic compounds which are useful for commercial applications may practically have an aromatic hydrocarbon ring, a 5- or 6-membered heterocyclic ring or a condensed heterocyclic ring. Among them, a compound having an aromatic hydrocarbon ring containing 6 to 14 carbon atoms, in particular an aromatic hydrocarbon ring with 6 to 10 carbon atoms (specifically, a benzene ring or a naphthalene ring) are desirable.

The process of the invention insures efficient oxidation of the methyl group or methylene group of the aromatic compound. Therefore, the number of a substituted methyl group(s) or methylene group(s) is not particularly restricted, and is selected from a broad range (e.g., about 1 to 10, and preferably about 1 to 8) depending on the species or size of the aromatic ring.

(d1) Aromatic compound substituted with a methyl group

The aromatic compound having a methyl group includes, for instance, an aromatic hydrocarbon substituted with about one to six methyl groups [e.g., toluene, o-, m-, or p-xylene, 1,2,3-trimethylbenzene, 1,2,4-trimethylbenzene, 1,3,5-trimethylbenzene (mesitylene), 1,2,3,4-tetramethylbenzene, 1,2,3,5-tetramethylbenzene, 1,2,4,5-tetramethylbenzene (durene), 1,2,3,4,5,6-hexamethylbenzene, 1-methylnaphthalene, 2-methylnaphthalene, 1,5-dimethylnaphthalene, 2,5-dimethylnaphthalene, methylanthracene, dimethylanthracene, trimethylanthracene, 4,4'-dimethylbiphenyl], a heterocyclic compound substituted with about one to six methyl groups [e.g., 2-methylfuran, 3-methylfuran, 2-methylpyran, 3-methylpyran, 4-methylpyran, 3,4-dimethylpyran, 4-methylchromene, 6-methylchroman, 2-methylpyridine, 3-methylpyridine, 4-methylpyridine, and other picolines, 2,3-dimethylpyridine, 2,4-dimethylpyridine, 2,5-dimethylpyridine, 3,5-dimethylpyridine and other lutidines, 2,3,4-trimethylpyridine, 2,3,5-trimethylpyridine, 2,3,6-trimethylpyridine, 2,4,6-trimethylpyridine, and other collidines, 4-methylindole, 5-methylindole, 7-methylindole, methylquinoline], and so on.

A preferred aromatic compound may practically have 1 to 4 methyl groups (e.g., one or two methyl groups) substituted in the molecule. Among such compounds, $C_{6-10}$ aromatic hydrocarbons and heterocyclic compounds containing a 5- or 6-membered heterocycle each having about one to four methyl groups are practically useful for commercial production of carboxylic acids. In particular, benzene derivatives each having a methyl group are advantageously employed.

(d2) Compound having a methylene group in an adjacent position to the aromatic ring The compound having a methylene group in an adjacent position to the aromatic ring includes an aromatic compound having an alkyl group or a substituted alkyl group containing two or more carbon atoms, and an aromatic compound having a cyclic methylene group.

As the aromatic compounds each having an alkyl group or a substituted alkyl group, there may be mentioned an aromatic hydrocarbon having an alkyl group [e.g., ethylbenzene, propylbenzene, cumene, butylbenzene, isobutylbenzene, 1,4-diethylbenzene, 1-ethyl-4-pentylbenzene and other aromatic hydrocarbons having a $C_{2-6}$ alkyl group, dibenzyl, diphenylmethane, triphenylmethane, 1-benzylnaphthalene, and other aromatic hydrocarbons having a substituted alkyl group], and a heterocyclic compound having an alkyl group (e.g., ethylpyridine, isopropylpyridine, butylpyridine), typically speaking.

Examples of the aromatic compound having a cyclic methylene group include a condensed polycyclic aromatic hydrocarbon having a condensed 5- to 8-membered ring [e.g. dihydronaphthalene, indene, indane, tetralin, fluorene, phenalene, α-tetralone, β-tetralone, indanone] and the like.

The aromatic compound (d) may have a methylene group together with a methyl group in an adjacent position to the aromatic ring, as well. As examples of such a compound, there may be mentioned alkyl-substituted hydrocarbons having at least one methyl group and at least one $C_{2-10}$ alkyl group [e.g., 1-methyl-2-ethylbenzene, 1-methyl-3-ethylbenzene, 1-methyl-4-ethylbenzene, 1-methyl-3-isopropylbenzene, 1-methyl-4-isopropylbenzene (cymene), 1-methyl-4-propylbenzene, 1-methyl-4-butylbenzene, 1-methyl-4-t-butylbenzene, 1,2-dimethyl-3-ethylbenzene, 1,2-dimethyl-4-ethylbenzene, 1,3-dimethyl-5-ethylbenzene, 1,3-dimethyl-4-ethylbenzene, 1,3-di-methyl-2-ethylbenzene, 1,4-dimethyl-2-ethylbenzene, 1-methyl-2-ethylnaphthalene, and other alkyl-substituted hydrocarbons having a methyl group and a $C_{2-6}$ alkyl group], alkyl-substituted heterocyclic compounds [e.g., 2-ethyl-4-methylpyridine, 3-ethyl-4-methylpyridine, 4-ethyl-2-methylpyridine], hydrocarbons having at least one methyl group and a cyclic methylene group (e.g., 3-methylindene), and so on.

These aromatic compounds may have other substituents besides the methyl group or methylene group, as well. Such aromatic compounds include carboxyl group-substituted hydrocarbons [e.g., 4-methylbenzoic acid, 1,2-dimethylbenzene-4-carboxylic acid], halogen-containing hydrocarbons [e.g., 4-chloro-1-methylbenzene, 3,4,5,6-tetrachloro-1,2-dimethylbenzene, 3,4,5,6-tetrabromo-1,2-dimethylbenzene], hydroxyl group-containing hydrocarbons (e.g., cresols such as o-, m- or p-cresol, 2,3-xylenol, thymol), aromatic hydrocarbons having a protected hydroxyl group [e.g., alkoxy group-containing hydrocarbons (e.g., 2-methoxy-1-methylbenzene, 3-methoxy-1-methylbenzene, 4-methoxy-1-methylbenzene, 4-ethoxy-1-methylbenzene, 4-isopropoxy-1-methylbenzene), acyloxy group-substituted hydrocarbons (e.g., 2-acetyloxy-1-methylbenzene, 3-acetyloxy-1-methylbenzene, 4-acetyloxy-1-methylbenzene, 4-propionyloxy-1-methylbenzene, 4-butyryloxy-1-methylbenzene)], amino group-containing hydrocarbons each of which may have a substituent [e.g., 4-amino-1-methylbenzene, 4-dimethylamino-1-methylbenzene], and other aromatic hydrocarbons, halogen-containing pyridine derivatives (e.g., 2-chloro-4-methylpyridine), and other heterocyclic compounds.

Oxidation of such an aromatic compound on contact with oxygen in the presence of the oxidation catalytic system (A)

or (B) insures oxidation of the methyl group or the adjacent methylene group to the aromatic ring with greatly high efficiency. Thus, an aldehyde, in particular, a carboxyl group-containing aromatic compound can be obtained from the aromatic compound having a methyl group, and a ketone can be prepared from the methylene group-containing aromatic compound with high selectively and an excellent yield. In particular, such an oxidation process insures smooth progress of the reaction in a short period, and provides a carboxyl group-containing aromatic compound or a ketone with high selectivity in a high yield, even in mild conditions. Further, when an aromatic compound having plural methyl groups is oxidized, it is easy to form a polycarboxylic acid having two or more carboxyl groups. Therefore, the process of the invention is useful for the production of a carboxyl group-containing aromatic compound or a ketone by contacting an aromatic compound having at least one methyl group or methylene group with oxygen. A preferred embodiment of the process of the invention includes a process of contacting a benzene derivative having a methyl group (e.g., toluene, xylene) with oxygen to produce a benzene derivative having a carboxyl group (e.g., benzoic acid, phthalic acid, isophthalic acid, terephthalic acid), which is useful for commercial applications, and a process of contacting a $C_{2-6}$ alkyl group-substituted aromatic hydrocarbon (e.g. ethylbenzene) with oxygen to give a carbonyl group-containing benzene derivative (e.g., acetophenone), which is also a commercially useful compound.

Accordingly, the process of the invention is effective for oxidation of the aromatic compound in mild conditions with high transformation rate and selectivity to give a carboxyl group-containing aromatic compound such as a monocarboxylic acid or polycarboxylic acid, or a ketone. In especial, the process is extremely useful for the production of an aromatic monocarboxylic acid inclusive of benzoic acid, or an aromatic polycarboxylic acid (in particular, an aromatic dicarboxylic acid) which is used as a raw material for the production of polyester or polyamide.

The use of the divalent transition metal compound (e.g., a divalent cobalt compound or a divalent manganese compound) as one component of the co-catalyst insures enhanced selectivity and yield of the polycarboxylic acid or ketone, even in such mild conditions as a low temperature (e.g., about 10 to 60° C.), in particular room temperature (about 15 to 30° C.). In particular, a combination of a compound containing Group 7 elements (e.g., Mn) of the Periodic Table of Elements and a compound containing Group 9 elements (e.g., Co) of the Periodic Table of Elements is advantageous. A combination of a further compound containing Group 11 elements (e.g., Cu) of the Periodic Table of Elements can enhance the selectivity and stabilize the catalytic system.

(e) Conjugate compound

The conjugate compound includes, for instance, a conjugate diene, an α,β-unsaturated nitrile or a α,β-unsaturated carboxylic acid or its derivative. It should be understood that the term "conjugate compound" means and includes not only compounds which have a double bond and a single bond alternately (e.g., butadiene), but also compounds which have unsaturated bonds (a double bond and/or a triple bond) alternately with or without putting a single bond between them (e.g., conjugated polyene). Therefore, a unsaturated diol is as far as a compound corresponding to the "conjugated diene", not only a unsaturated diol having sole double bonds but also a unsaturated diol having plural double bonds or triple bonds are given a general name "alkene diol". Furthermore, "acrylic acid, meta acrylic acid or derivatives thereof" sometimes give a general name to "(meta)acrylic acid or its derivative".

As the conjugate dienes, there may be exemplified compounds each having a conjugate double bond such as butadiene (1,3-butadiene) and isoprene (2-methyl-1,3-butadiene), compounds having a double bond and a triple bond (e.g., vinylacetylene, divinylacetylene) and derivatives of these compounds. Examples of the derivatives of the conjugate diene include 2-chlorobutadiene, 2,3-dichlorobutadiene, and other compounds having a halogen atom (iodine, bromine, chlorine, or fluorine atom), 2-ethylbutadiene, 2,3-dimethylbutadiene, and other compounds having an alkyl group (e.g., methyl, ethyl, propyl, isopropyl, butyl, isobutyl, sec-butyl, t-butyl, and other lower alkyl groups having about one to four carbon atoms), butadiene-1-carboxylic acid and other compounds each having a carboxyl group. A preferred conjugate diene includes butadiene and isoprene.

Oxidation, which is employed the oxidation catalytic system (A) or (B), of the conjugate diene with oxygen provides an alkenediol. The substituted positions of hydroxyl groups of the produced alkenediol are not strictly limited as far as it being a diol corresponding to the conjugate diene. By way of example, a butenediol formed by oxidation of butadiene may be any of the 2-butene-1,4-diol or 1-butene-3,4-diol, and it may be either a cis-form or trans-form.

The α,β-unsaturated nitrile includes (meth)acrylonitrile, typically speaking.

Examples of the α,β-unsaturated carboxylic acid or its derivative include (meth)acrylic acid; methyl (meth) acrylate, ethyl (meth)acrylate, isopropyl (meth)acrylate, n-butyl (meth)acrylate, isobutyl (meth)acrylate, hexyl (meth)acrylate, 2-ethylhexyl (meth)acrylate, lauryl (meth) acrylate, and other alkyl (meth)acrylates; 2-hydroxyethyl (meth)acrylate, 2-hydroxypropyl (meth)acrylate, and other hydroxyalkyl (meth)acrylates; glycidyl (meth)acrylate; dimethylaminoethyl (meth)acrylate, diethylaminoethyl (meth) acrylate; (meth)acrylamide, N-methyl(meth)acrylamide, N-methylol(meth)acrylamide, and other (meth)acrylamide derivatives, and the like.

Oxidation of the α,β-unsaturated nitrile, α,β-unsaturated carboxylic acid or its derivative on contact with oxygen in the presence of the oxidation catalytic system (A) or (B) insures selective oxidation of the α,β-unsaturated bond to give a diol, an aldehyde or derivatives thereof. The use of a protonic solvent (e.g., acetic acid, propionic acid or other organic acids, methanol, ethanol, n-propanol, isopropanol, n-butanol, t-butanol, or other alcohols) as a reaction solvent may sometimes provide a diol derivative inclusive of an acetal or acyloxy compound. The aldehyde or its derivative, or a diol derivative inclusive of an acetal is an equivalent compound to the diol. For instance, oxidation of acrylonitrile with the use of an alcohol (e.g., methanol) as the reaction solvent sometimes provides a 1,1-dialkoxypropionitrile (e.g., 1,1-dimethoxypropionitrile). Further, a methyl 1,1-dialkoxypropionate (e.g., methyl 1,1-dimethoxypropionate) occasionally forms when methyl acrylate is oxidized in an alcohol (e.g., methanol) solvent.

(f) Other substrates

As the other substrates, there may be exemplified with a heterocyclic compound having a methylene group (f1), a chain hydrocarbon having a methine carbon atom (a methylidyne group) (f2), a compound having a methylene group in an adjacent position to an unsaturated bond (f3), and a compound having a methylene group in an adjacent position to a carbonyl group (f4).

(f1) Heterocyclic compound having a methylene group

The heterocyclic compound having a methylene group includes a 5- or 6-membered cyclic compound having a hetero-atom selected from a nitrogen atom, an oxygen atom or a sulfur atom, or a condensed heterocyclic compound in which a 5- or 6-membered ring having a hetero-atom is condensed to an aromatic ring. An example of such compound includes dihydrofuran, tetrahydrofuran, pyran, dihydropyran, tetrahydropyran, piperidine, piperazine, pyrrolidine, xanthene, and the like. Oxidation of these substrates in the presence of the catalytic system (A) or (B) insures an efficient introduction of an oxo group or a hydroxyl group into a methylene group.

(f2) Chain hydrocarbon having a methine carbon atom (a methylidyne group)

As examples of the chain hydrocarbon having a methine carbon atom, there may be mentioned chain hydrocarbons each having a tertiary carbon atom, such as isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane, 2-methylnonane, and other aliphatic hydrocarbons each having about 4 to 10 carbon atoms. Oxidation of these substrates with oxygen in the presence of the catalytic system (A) or (B) provides a compound substituted hydroxyl group on a methyne carbon atom efficiently.

(f3) Compound having a methylene group in an adjacent position to an unsaturated bond The compound (f3) includes, for instance, chain unsaturated hydrocarbons each having about 3 to 12 carbon atoms as well as having a double bond and/or a triple bond, such as propylene, 1-butene, 2-butene, butadiene, 1-pentene, 2-pentene, isoprene, 1-hexene, 2-hexene, 1,5-hexadiene, 2,3-dimethyl-2-butene, 3-hexene, 1-heptene, 2-heptene, 1,6-heptadiene, 1-octene, 2-octene, 3-octene, 1,7-octadiene, 2,6-octadiene, 2-methyl-2-butene, 1-nonene, 2-nonene, decene (decaene), decadiene, dodecene, dodecadiene, dodecatriene, undecene, undecadiene, undecatriene, and so forth. Oxidation of these substrates using the oxidation catalytic system (A) or (B) provides corresponding oxides (e.g., ketones, alcohols, aldehydes and carboxylic acids) with high yields.

(f4) Compound having a methylene group in an adjacent position to a carbonyl group Examples of the compound having an (active) methylene group in an adjacent position to a carbonyl group include aldehydes, ketones, carboxylic acids or their derivatives.

The aldehyde includes, for instance, aliphatic aldehydes (e.g., acetaldehyde, propionaldehyde, butyraldehyde, isobutyraldehyde, pentylaldehyde, hexylaldehyde, heptylaldehyde, octylaldehyde, nonylaldehyde, decylaldehyde, and other $C_{2-12}$ alkylmonoaldehydes, malonaldehyde, succinaldehyde, adipinaldehyde, sebacaldehyde, and other aliphatic polyaldehydes), aromatic aldehydes (e.g., benzaldehyde, anisaldehyde), alicyclic aldehydes (e.g., formylcyclohexane, cycloneral), and heterocyclic aldehydes (e.g., nicotinaldehyde, furfural).

As examples of the ketone, there may be mentioned aliphatic ketones (e.g., acetone, methyl ethyl ketone, methyl isopropyl ketone, methyl isobutyl ketone, methyl t-butyl ketone, 2-pentanone, 3-pentanone, 2-hexanone, 3-hexanone, 2-heptanone, 3-heptanone, 4-heptanone, 2-octanone, 3-octanone, 4-octanone, 2-nonanone, 2-decanone), aromatic ketones (e.g., acetophenone, propiophenone) and so on.

The illustrative carboxylic acid or its derivative includes aliphatic dicarboxylic acids or their derivatives (e.g., malonic acid or its ester, succinic acid or its ester, glutaric acid or its ester).

Oxidation of these carbonyl compounds with oxygen in the presence of the oxidation catalytic system (A) or (B) provides corresponding oxides (e.g., ketones, alcohols, aldehydes and carboxylic acids) efficiently.

Oxidation Reaction

The oxygen used in oxidation of the substrate may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoints of handling property and safety, and economical property.

An amount of oxygen can be selected from a range according to the species of the substrate, and usually is, 0.5 mole or more (e.g., 1 mole or more), preferably about 1 to 100 moles, and more preferably about 2 to 50 moles relative to 1 mole of the substrate. The oxygen is practically used in an excess mole relative to the substrate. In specific, the reaction is advantageously carried out in an atmosphere containing molecular oxygen such as air or oxygen gas.

Oxidation process of the invention is generally conducted in an inert organic solvent. As the organic solvents, both a protic solvent and a non-protic solvent can be employed. As the protic solvent, there may be mentioned, for example, formic acid, acetic acid, propionic acid and other organic carboxylic acids , t-butanol, t-amyl alcohol and other alcohols. Both polar and non-polar solvents can be employed as non-protic solvents. As the non-protic solvent, there may be mentioned, for example, a non-protonic nonpolar solvent (e.g., an aliphatic hydrocarbon such as hexane and octane, an aromatic hydrocarbon such as benzene, a halogenated hydrocarbon such as chloroform, dichloromethane, dichloroethane, tetrachlorocarbon and chlorobenzene), a non-protonic polar solvent (e.g., nitrobenzene, nitromethane, nitroethane and other nitro compounds, ethyl acetate, butyl acetate and other esters, dimethylether, diethylether, diisopropylether, dioxane and other ethers, acetonitrile, propionitrile, benzonitrile and other nitriles, formamide, acetamide, dimethylformamide (DMF), dimethylacetamide and other amides). These solvents can be employed independently or as a mixture of 2 or more. Incidentally, the substrate may be employed as the reaction solvent, if used in an excess amount. Use may practically be made of, as the solvent, acetic acid or other organic acids, acetonitrile, benzonitrile or other nitriles.

The reaction in the presence of a protonic acid results in smooth oxidation, and it provides an object compound with high selectivity in a high yield. The protonic acid may also be used as the solvent as described above. As the protonic acid, there may be exemplified organic acids (e.g., formic acid, acetic acid, propionic acid and other organic carboxylic acids, oxalic acid, succinic acid, tartaric acid and other hydroxycarboxylic acids, methanesulfonic acid, ethanesulfonic acid and other alkylsulfonic acids, benzenesulfonic acid, p-toluenesulfonic acid and other arylsulfonic acids), and inorganic acids (e.g., hydrochloric acid, sulfuric acid, nitric acid, phosphoric acid).

In the presence of the non-protic solvent (in particular, in the coexicisting of the oxidation catalytic system (B)), oxidation of a non aromatic cyclic compound, such as cycloalkane, inhibits the formation of a dicarboxylic acid and provides a ketone or an alcohol with high selectivity.

The process of the invention is characterized in that the oxidation reaction smoothly proceeds even in comparatively mild or moderate conditions. A reaction temperature can be voluntarily selected according to the species of the substrate and the catalytic system. The temperature is, for instance, about 0 to 300° C., preferably about 30 to 250° C., more preferably about 50 to 200° C., and practically about 70 to 150° C. As described above, depending on the species of the oxidation catalytic system, the oxidation reaction can smoothly proceed even at a comparatively low temperature such as room temperature.

The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm. A reaction time can be liberally chosen within a range of about 30 minutes to 48 hours, preferably about 1 to 36 hours, and more preferably about 2 to 24 hours, depending on the reaction temperature and pressure.

The reaction may be effected in a conventional manner such as in a batch system, semi-batch system or continuous system, in the presence of molecular oxygen or under flow of molecular oxygen. After completion of the reaction, a reaction product can easily be isolated and purified according to a conventional technology, such as filtration, condensation, distillation, extraction, crystallization, recrystallization, column chromatography, or other isolation means, or a combination of these technologies.

The present invention does not specifically require treatment of an exhaust gas, enhances the catalytic activities in the oxidation with oxygen or the oxidation with air, and insures efficient oxidation of the substrate because that the oxidation catalytic system is constituted an imide compound and a co-catalyst comprising specific plural elements or compounds. Further, high activities can be maintained with inhibiting the deactivation of imide compounds. Therefore, the substrates are oxidized with oxygen or with air to give corresponding ketones, alcohols, aldehydes, or carboxylic acids to the substrates with a high conversion and selectivity.

The following examples are intended to describe the present invention in more detail, but should by no means be construed to limit the scope of the invention.

EXAMPLES

Example 1

To 25 ml of acetic acid were added 10 mmol of cyclohexane, 1 mmol of N-hydroxyphthalimide and a trinary co-catalyst [0.01 mmol of acetylacetonatomanganese $Mn(AA)_2$, 0.1 mmol of acetylacetonatoiron $Fe(AA)_3$ and 0.01 mmol of acetylacetonatocobalt $Co(AA)_2$]and the resultant mixture was stirred under an oxygen atmosphere at a temperature of 100° C. for 6 hours. The products in the reaction mixture were analyzed by gas chromatography, and, as a result, cyclohexane was converted into adipic acid with a conversion of 89% (yield 70%).

Example 2

The reaction was conducted in the same manner as Example 1 except using a trinary co-catalyst [0.01 mmol of acetylacetonatomanganese $Mn(AA)_2$, 0.04 mmol of acetylacetonatoiron $Fe(AA)_3$ and 0.01 mmol of acetylacetonatocobalt $Co(AA)_2$] instead of the trinary co-catalyst of Example 1, and cyclohexane was converted into adipic acid (yield 56%) and cyclohexanone (yield 6%) with a conversion of 77%.

Example 3

The reaction was conducted in the same manner as Example 1 except using a trinary co-catalyst [0.002 mmol of acetylacetonatomanganese $Mn(AA)_2$, 0.02 mmol of acetylacetonatoiron $Fe(AA)_3$ and 0.002 mmol of acetylacetonatocobalt $Co(AA)_2$] instead of the trinary co-catalyst of Example 1, and cyclohexane was converted into adipic acid (yield 34%) and cyclohexanone (yield 7%) with a conversion of 50%.

Example 4

The reaction was conducted in the same manner as Example 1 except using a trinary co-catalyst [0.01 mmol of acetylacetonatomanganese $Mn(AA)_2$, 0.1 mmol of ruthenium chloride $RuCl_3$ and 0.01 mmol of acetylacetonatocobalt $Co(AA)_2$] instead of the trinary co-catalyst of Example 1, and cyclohexane was converted into adipic acid (yield 76%) and cyclohexanone (yield 2%) with a conversion of 90%.

Example 5

The reaction was conducted in the same manner as Example 1 except using a trinary co-catalyst [0.01 mmol of acetylacetonatomanganese $Mn(AA)_{2, 0.1}$ mmol of cupric chloride $CuCl_2$ and 0.01 mmol of acetylacetonatocobalt $Co(AA)_2$] instead of the trinary co-catalyst of Example 1, and cyclohexane was converted into adipic acid (yield 52%) and cyclohexanone (yield 4%) with a conversion of 62%.

Example 6

To 25 ml of acetic acid were added 10 mmol of adamantane, 1 mmol of N-hydroxyphthalimide and a binary co-catalyst [0.1 mmol of acetylacetonatocobalt $Co(AA)_3$ and 0.4 mmol of acetylacetonatoiron $Fe(AA)_3$]and the resultant mixture was stirred under an oxygen atmosphere at a temperature of 75° C. for 6 hours. The products in the reaction mixture were analyzed by gas chromatography, and, as a result, adamantane was converted into 1-adamantanol (yield 39%) , 1,3-adamantanediol (yield 49%) and adamantanone (yield 6%) with a conversion of 99%.

Example 7

The reaction was conducted in the same manner as Example 6 except using a binary co-catalyst [0.1 mmol of acetylacetonatocobalt $Co(AA)_3$ and 0.4 mmol of cupric acetate $Cu(OAc)_2$] instead of the binary co-catalyst of Example 6, and adamantane was converted into 1-adamantanol (yield 67%), 1,3-adamantanediol (yield 18%) and adamantanone (yield 6%) with a conversion of 93%.

Example 8

The reaction was conducted in the same manner as Example 6 except using a binary co-catalyst [0.03 mmol of acetylacetonatovanadium $V(AA)_3$ and 0.02 mmol of cupric bromide CuBr] instead of the binary co-catalyst of Example 6, and adamantane was converted into 1-adamantanol (yield 74%) and adamantanone (yield 6%) with a conversion of 82%. The selectivity of such oxides (the alcohol and the ketone) was 98%.

Example 9

The reaction was conducted in the same manner as Example 6 except using a binary co-catalyst [0.03 mmol of acetylacetonatovanadium V(AA)$_3$ and 0.02 mmol of acetylacetonatocopper Cu(AA)$_2$] instead of the binary co-catalyst of Example 6, and adamantane was converted into 1-adamantanol (yield 84%) and adamantanone (yield 7%) with a conversion of 93%. The selectivity of such oxides (the alcohol and the ketone) was 98%.

Example 10

To 25 ml of acetic acid were added 10 mmol of adamantane, 1 mmol of N-hydroxyphthalimide and a binary co-catalyst [0.03 mmol of acetylacetonatovanadium V(AA)$_3$ and 0.02 mmol of acetylacetonatomanganese Mn(AA)$_3$] and the resultant mixture was stirred under an oxygen atmosphere at a temperature of 75° C. for 6 hours. The products in the reaction mixture were analyzed by gas chromatography, and, as a result, adamantane was converted into 1-adamantanol (yield 37%), 1,3-adamantanediol (yield 35%), 1,3,5-adamantanetriol (yield 5%) and 1,3,5,7-adamantanetetraol (yield 4%) with a conversion of 100%.

Example 11

To 25 ml of acetic acid were added 10 mmol of adamantane, 1 mmol of N-hydroxyphthalimide and a binary co-catalyst [0.03 mmol of acetylacetonatovanadium V(AA)$_3$ and 0.02 mmol of molibdic acid H$_2$MoO$_4$] and the resultant mixture was stirred under an oxygen atmosphere at a temperature of 75° C. for 6 hours. The products in the reaction mixture were analyzed by gas chromatography, and, as a result, adamantane was converted into 1-adamantanol (yield 18%), 1,3-adamantanediol (yield 36%), 1,3,5-adamantanetriol (yield 7%) and 1,3,5,7-adamantanetetraol (yield 7%) with a conversion of 97%.

Example 12

To 25 ml of acetic acid were added 10 mmol of adamantane, 1 mmol of N-hydroxyphthalimide and a binary co-catalyst [0.03 mmol of acetylacetonatovanadium V(AA)$_3$ and 0.02 mmol of molibdic acid H$_2$MoO$_4$] and the resultant mixture was stirred under an oxygen atmosphere at a temperature of 75° C. for 3 hours. The products in the reaction mixture were analyzed by liqiud chromatography, and, as a result, adamantane was converted into 1-adamantanol (yield 53%), 1,3-adamantanediol (yield 23%), 1,3,5-adamantanetriol (yield 1%) and 1,3,5,7-adamantanetetraol (yield 9%) with a conversion of 89%. In the reaction mixture, 59% of N-hydroxyphthalimide was remained.

Example 13

The reaction was conducted in the same manner as Example 6 except using a binary co-catalyst [0.03 mmol of acetylacetonatovanadium V(AA)$_3$ and 0.02 mmol of acetylacetonatonickel Ni(AA)$_2$] instead of the binary co-catalyst of Example 6, and adamantane was converted into 1-adamantanol (yield 74%) and adamantanone (yield 6%) with a conversion of 100%. The selectivity of such oxides (the alcohol and the ketone) was 80%.

Example 14

To 25 ml of acetic acid were added 10 mmol of fluorene, 1 mmol of N-hydroxyphthalimide and a binary co-catalyst [0.03 mmol of acetylacetonatovanadium V(AA)$_3$ and 0.02 mmol of acetylacetonatocopper Cu(AA)$_2$]and the resultant mixture was stirred under an oxygen atmosphere at a temperature of 90° C. for 8 hours. The products in the reaction mixture were analyzed by gas chromatography, and, as a result, fluorene was converted into fluorenol (yield 5%) and fluorenone (yield 30%) with a conversion of 36%. The selectivity of such oxides (the alcohol and the ketone) was 97%.

Example 15

To 25 ml of acetonitrile were added 10 mmol of durene, 1 mmol of N-hydroxyphthalimide and a binary co-catalyst [0.04 mmol of cupric acetate Cu(OAc)$_2$ and 0.005 mmol of acetylacetonatocobalt Co(AA)$_2$] and the resultant mixture was stirred under an oxygen atmosphere at a temperature of 70° C. for 3 hours. The products in the reaction mixture were analyzed by gas chromatography, and, as a result, durene was converted into 2,4,5-trimethylbenzaldehyde (yield 28%) and 2,4,5-trimethylbenzoic acid (yield 32%) with a conversion of 69%.

Example 16

The reaction was conducted in the same manner as Example 15 except using a binary co-catalyst [0.04 mmol of cupric acetate Cu(OAc)$_2$ and 0.005 mmol of acetylacetonatomanganese Mn(AA)$_2$] instead of the binary co-catalyst of Example 15, and durene was converted into 2,4,5-trimethylbenzaldehyde (yield 18%) and 2,4,5-trimethylbenzoic acid (yield 66%) with a conversion of 92%.

Example 17

The reaction was conducted in the same manner as Example 15 except using a binary co-catalyst [0.04 mmol of acetylacetonatocobalt Co(AA)$_2$ and 0.005 mmol of acetylacetonatomanganese Mn(AA)$_2$] instead of the binary co-catalyst of Example 15, and durene was converted into 2,4,5-trimethylbenzaldehyde (yield 20%) and 2,4,5-trimethylbenzoic acid (yield 58%) with a conversion of 93%.

Example 18

To 25 ml of acetic acid were added 10 mmol of mesitylene, 1 mmol of N-hydroxyphthalimide and a binary co-catalyst [0.04 mmol of acetylacetonatocobalt Co(AA)$_2$ and 0.005 mmol of acetylacetonatomanganese Mn(AA)$_2$] and the resultant mixture was stirred under an oxygen atmosphere at a temperature of 70° C. for 3 hours. The products in the reaction mixture were analyzed by gas chromatography, and, as a result, mesitylene was converted into 3,5-dimethylbenzaldehyde (yield 17%) and 3,5-dimethylbenzoic acid (yield 17%) with a conversion of 60%.

Example 19

The reaction was conducted in the same manner as Example 18 except that the reaction temperature was changed to a temperature of 100° C., and, as a result, mesitylene was converted into 3,5-dimethylbenzaldehyde (yield 14%) and 3,5-dimethylbenzoic acid (yield 71%) with a conversion of 91%.

Example 20

The reaction was conducted in the same manner as Example 18 except using 0.5 mmol of N-hydroyphthalimide and a binary co-catalyst [0.04 mmol of acetylacetonatocobalt Co(AA)$_2$ and 0.01 mmol of acetylacetonatomanganese Mn(AA)$_2$] instead of 1 mmol of N-hydroxyphthalimide and the binary co-catalyst of Example 18, and mesitylene was converted into 3,5-dimethylbenzaldehyde (yield 22%) and 3,5-dimethylbenzoic acid (yield 37%) with a conversion of 71%.

Example 21

To 25 ml of acetonitrile were added 10 mmol of mesitylene, 1 mmol of N-hydroxyphthalimide and a binary co-catalyst [0.04 mmol of acetylacetonatocopper Cu(AA)$_2$ and 0.005 mmol of acetylacetonatocobalt Co(AA)$_2$] and the resultant mixture was stirred under an oxygen atmosphere at a temperature of 70° C. for 3 hours. The products in the reaction mixture were analyzed by gas chromatography, and, as a result, mesitylene was converted into 3,5-dimethylbenzaldehyde (yield 19%) and 3,5-dimethylbenzoic acid (yield 52%) with a conversion of 73%.

Example 22

The reaction was conducted in the same manner as Example 21 except using a binary co-catalyst [0.04 mmol of cupric acetate Cu(OAc)$_2$ and 0.005 mmol of acetylacetonatomanganese Mn(AA)$_2$] instead of the binary co-catalyst of Example 21, and mesitylene was converted into 3,5-dimethylbenzaldehyde (yield 23%) and 3,5-dimethylbenzoic acid (yield 34%) with a conversion of 67%.

Example 23

The reaction was conducted in the same manner as Example 21 except using a trinary co-catalyst [0.04 mmol of cupric acetate Cu(OAc)$_2$, 0.005 mmol of acetylacetontaocobalt Co(AA)$_2$ and 0.01 mmol of acetylacetonatomanganese Mn(AA)$_2$] instead of the binary co-catalyst of Example 21, and mesitylene was converted into 3,5-dimethylbenzaldehyde (yield 16%) and 3,5-dimethylbenzoic acid (yield 62%) with a conversion of 81%.

Example 24

The reaction was conducted in the same manner as Example 21 except using a trinary co-catalyst [0.04 mmol of cupric acetate Cu(OAc)$_2$0.005 mmol of acetylacetontaocobalt Co(AA)$_2$ and 0.005 mmol of acetylacetonatomanganese Mn(AA)$_2$] instead of the binary co-catalyst of Example 21, and mesitylene was converted into 3,5-dimethylbenzaldehyde (yield 22%) and 3,5-dimethylbenzoic acid (yield 37%) with a conversion of 67%.

Example 25

To 25 ml of acetic acid were added 10 mmol of mesitylene, 1 mmol of N-hydroxyphthalimide and a binary co-catalyst [0.04 mmol of acetylacetonatocobalt Co(AA)$_2$ and 0.005 mmol of acetylacetonatomanganese Mn(AA)$_2$] and the resultant mixture was stirred under an oxygen atmosphere at a temperature of 70° C. for 3 hours. The products in the reaction mixture were analyzed by gas chromatography, and, as a result, mesitylene was converted into 3,5-dimethylbenzaldehyde (yield 14%) and 3,5-dimethylbenzoic acid (yield 71%) with a conversion of 91%.

Example 26

The reaction was conducted in the same manner as Example 25 except that the reaction time was changed to 6 hours, and mesitylene was converted into 3,5-dimethylbenzaldehyde (yield 13%) and 3,5-dimethylbenzoic acid (yield 68%) with a conversion of 91%.

Example 27

To 20 ml of benzonitrile were added 10 mmol of cyclohexane, 1 mmol of N-hydroxyphthalimide, 0.01 mmol of cobalt acetate Co(OAc)$_2$, and 0.05 mmol of acetylacetonatocobalt Co(AA)$_2$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 10%) and cyclohexanol (yield 1%) with a conversion of 12%. Adipic acid was not detected. The selectivity of K/A oil was 93% based on the consumed cyclohexane.

Example 28

The reaction was conducted in the same manner as Example 27 except using 10 ml of benzonitrile instead of 20 ml of benzonitrile of Example 27, and cyclohexane was converted into cyclohexanone (yield 19%), cyclohexanol (yield 0.8%) and adipic acid (yield 2%) with a conversion of 24%. The selectivity of K/A oil and adipic acid was 83% and 8%, respectively, based on the consumed cyclohexane.

Example 29

The reaction was conducted in the same manner as Example 27 except using 10 ml of benzonitrile and 0.1 mmol of acetylacetonatocobalt Co(AA)$_3$ instead of 20 ml of benzonitrile and 0.05 mmol of acetylacetonatocobalt of Example 27, and cyclohexane was converted into cyclohexanone (yield 22%), cyclohexanol (yield 0.8%) and adipic acid (yield 3%) with a conversion of 33%. The selectivity of K/A oil and adipic acid was 70% and 9%, respectively, based on the consumed cyclohexane.

Example 30

The reaction was conducted in the same manner as Example 27 except using 10 ml of benzonitrile, 0.05 mmol of cobalt acetate Co(OAc)$_2$ and 0.1 mmol of acetylacetonatocobalt Co(AA)$_3$ instead of 20 ml of benzonitrile, 0.01 mmol of cobalt acetate Co(OAc)$_2$ and 0.05 mmol of acetylacetonatocobalt of Example 27, and cyclohexane was converted into cyclohexanone (yield 23%), cyclohexanol (yield 0.7%) and adipic acid (yield 2.9%) with a conversion of 32%. The selectivity of K/A oil and adipic acid was 74% and 9%, respectively, based on the consumed cyclohexane.

Example 31

The reaction was conducted in the same manner as Example 27 except that stirring was effected at a temperature of 65° C. and that benzonitrile 10 ml was used instead of benzonitrile 20 ml of Example 27, and cyclohexane was converted into K/A oil in the total yield of 13%. The selectivity of K/A oil was 85% based on the consumed cyclohexane.

Example 32

The reaction was conducted in the same manner as Example 27 except that stirring was effected at a temperature of 85° C. and that benzonitrile 10 ml was used instead of benzonitrile 20 ml of Example 27, and cyclohexane was converted into K/A oil in the total yield of 20%. The selectivity of K/A oil was 54% based on the consumed cyclohexane.

Example 33

The reaction was conducted in the same manner as Example 27 except using 0.1 mmol of acetylacetonatocobalt Co(AA)$_3$ instead of 0.01 mmol of it, and cyclohexane was converted into K/A oil in the total yield of 12%. The selectivity of K/A oil, cyclohexane bases, was 90%.

Example 34

The reaction was conducted in the same manner as Example 27 except using 5 ml of benzonitrile and 0.1 mmol of acetylacetonatocobalt Co(AA)$_3$ instead of 20 ml of benzonitrile and 0.01 mmol of acetylacetonatocobalt Co(AA)$_3$, and cyclohexane was converted into K/A oil in the total yield of 23%. The selectivity of K/A oil was 58% based on the consumed cyclohexane.

Example 35

To 10 ml of benzonitrile were added 10 mmol of cyclohexane, 0.5 mmol of N-hydroxyphthalimide, 0.01 mmol of cobalt acetate Co(OAc)$_2$, and 0.1 mmol of acetylacetonatocobalt Co(AA)$_2$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 16%), cyclohexanol (yield 0.7%) and adipic acid (yield 3.2%) with a conversion of 24%. The selectivity of K/A oil was 70% based on the consumed cyclohexane.

Example 36

The reaction was conducted in the same manner as Example 35 except using 5 ml of benzonitrile instead of 10 ml of it, and cyclohexane was converted into cyclohexanone (yield 20%), cyclohexanol (yield 0.8%) and adipic acid (yield 3%) with the conversion of 25%. The selectivity of K/A oil was 84% based on the consumed cyclohexane.

Example 37

The reaction was conducted in the same manner as Example 35 except using 5 ml of benzonitrile and 0.05 mmol of acetylacetonatocobalt Co(AA)$_3$ instead of 10 ml of benzonitrile and 0.1 mmol of acetylacetonatocobalt Co(AA)$_3$, and cyclohexane was converted into cyclohexanone (yield 19%), cyclohexanol (yield 0.9%) and adipic acid (yield 2.8%) with the conversion of 25%. The selectivity of K/A oil was 80% based on the consumed cyclohexane.

Example 38

To 10 ml of benzonitrile were added 20 mmol of cyclohexane, 1 mmol of N-hydroxyphthalimide, 0.02 mmol of cobalt acetate Co(OAc)$_3$, and 0.1 mmol of acetylacetonatocobalt Co(AA)$_2$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 19%), cyclohexanol (yield 0.9%) and adipic acid (yield 2.5%) with a conversion of 25%. The selectivity of K/A oil was 80% based on the consumed cyclohexane.

Example 39

The reaction was conducted in the same manner as Example 38 except using 33 mmol of cyclohexane instead of 20 mmol of it, and cyclohexane was converted into cyclohexanone (yield 17%), cyclohexanol (yield 1%) and adipic acid (yield 3.2%) with the conversion of 24%. The selectivity of K/A oil was 75% based on the consumed cyclohexane.

Example 40

The reaction was conducted in the same manner as Example 38 except using 50 mmol of cyclohexane instead of 20 mmol of it, and cyclohexane was converted into cyclohexanone (yield 14%), cyclohexanol (yield 1%) and adipic acid (yield 2.7%) with the conversion of 21%. The selectivity of K/A oil was 71% based on the consumed cyclohexane.

Example 41

To 10 ml of acetonitrile were added 10 mmol of cyclohexane, 1 mmol of N-hydroxyphthalimide, 0.01 mmol of cobalt acetate Co(OAc)$_3$, and 0.1 mmol of acetylacetonatocobalt Co(AA)$_2$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 24%), cyclohexanol (yield 0.6%) and adipic acid (yield 3.9%) with a conversion of 34%. The selectivity of K/A oil and adipic acid was 72% and 11%, respectively, based on the consumed cyclohexane.

Example 42

To 10 ml of benzonitrile were added 10 mmol of cyclohexane, 1 mmol of N-hydroxyphthalimide, 0.01 mmol of cobalt acetate Co(OAc)$_2$, and 0.1 mmol of acetylacetonatochromium Cr(AA)$_3$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 10%), cyclohexanol (yield 0.8%) and adipic acid (trace amount) with a conversion of 33%.

Example 43

To 10 ml of benzonitrile were added 10 mmol of cyclohexane, 1 mmol of N-hydroxyphthalimide, 0.01 mmol of rhodium acetate [Rh(OAc)$_2$]$_2$, and 0.1 mmol of acetylacetonatocobalt Co(AA)$_3$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 11%), cyclohexanol (yield 0.9%) and adipic acid (trace amount) with a conversion of 16%.

Example 44

To 10 ml of benzonitrile were added 10 mmol of cyclohexane, 1 mmol of N-hydroxyphthalimide, 0.1 mmol of vanadyl acetylacetonato VO(AA)$_3$, and 0.1 mmol of acetylacetonatocobalt Co(AA)$_3$ and the resultant mixture was stirred under an oxygen atmosphere at a temperature of 75° C. for 16 hours. The products in the reaction imixture were analyzed by gas chromatography, and, as a result, cyclohexane was converted into cyclohexanone (yield 21%), cyclohexanol (yield 0.6%) and adipic acid (yield 4.5%) with a conversion of 35%. The selectivities of K/A oil and adipic acid was 62% and 13%, respectively, for consumed cyclohexane.

Comparative Example 1

To 20 ml of benzonitrile were added 10 mmol of cyclohexane, 1 mmol of N-hydroxyphthalimide and 0.05 mmol of cobalt acetate Co(OAc)$_2$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 5.2%), cyclohexanol (yield 0.6%) with a conversion of 6.3%. Adipic acid was not detected.

Comparative Example 2

To 20 ml of benzonitrile were added 10 mmol of cyclohexane, 1 mmol of N-hydroxyphthalimide and 0.05 mmol of acetylacetonatocobalt Co(AA)$_3$ and the resultant mixture was stirred under an oxygen atmosphere at a temperature of 75° C. for 16 hours. The products in the reaction mixture were analyzed by gas chromatography, and, as a result, cyclohexane was converted into cyclohexanone (yield 2.4%), cyclohexanol (yield 1%) with a conversion of not more than 5%. Adipic acid was not detected.

What is claimed is:

1. An oxidation catalytic system which comprises;
an imide compound shown by the following formula (1)

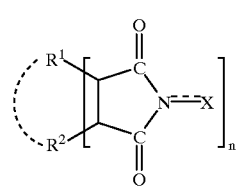

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring; X represents an oxygen atom or a hydroxyl group; and n denotes an integer of 1 to 3, and a co-catalyst comprising plural transition metal compounds excluding a polyacid.

2. An oxidation catalytic system according to claim 1, wherein said co-catalyst comprises a single compound containing plural elements selected from the group consisting of Group 4 elements, Group 5 elements, Group 6 elements, Group 7 elements, Group 8 elements, Group 9 elements, Group 10 elements and Group 11 elements of the Periodic Table of Elements, or plural compounds containing the elements selected from different Groups.

3. An oxidation catalytic system according to claim 1, wherein said co-catalyst comprises a single compound containing elements having plural different valencies selected from the same Group or plural compounds containing elements having different valancies selected from the same Group.

4. An oxidation catalytic system according to claim 3, wherein said valencies of elements in said compound(s) are 2 to 4.

5. An oxidation catalytic system according to claim 1, wherein said co-catalyst comprises plural compounds selected from the group consisting of an oxide, an organic acid salt, an inorganic acid salt, a halide, and a complex.

6. An oxidation catalytic system according to claim 1, wherein said co-catalyst comprises the following combination of an element or a compound;

(b) a combination of a Group 4 element of the Periodic Table of the Elements or compound thereof and at least one element selected from the group consisting of a Group 5 element, a Group 6 element, a Group 7 element, a Group 8 element, a Group 9 element, a Group 10 element and a Group 11 element of the Periodic Table of Elements or a compound thereof;

(c) a combination of a Group 5 element of the Periodic Table of the Elements or compound thereof and at least one element selected from the group consisting of a Group 6 element, a Group 7 element, a Group 8 element, a Group 9 element, a Group 10 element and a Group 11 element of the Periodic Table of Elements or a compound thereof;

(d) a combination of a Group 6 element of the Periodic Table of the Elements or compound thereof and at least one element selected from the group consisting of a Group 7 element, a Group 8 element, a Group 9 element, a Group 10 element, and a Group 11 element of the Periodic Table of Elements or a compound thereof;

(e) a combination of a Group 7 element of the Periodic Table of the Elements or compound thereof and at least one element selected from the group consisting of a Group 9 element, a Group 10 element and a Group 11 element of the Periodic Table of Elements or a compound thereof;

(f) a combination of a Group 8 element of the Periodic Table of the Elements or compound thereof and at least one element selected from the group consisting of a Group 9 element, a Group 10 element, and a Group 11 element of the Periodic Table of Elements or a compound thereof;

(g) a combination of a Group 9 element of the Periodic Table of the Elements or compound thereof and at least one element selected from the group consisting of a Group 10 element and a Group 11 element of the Periodic Table of Elements or a compound thereof;

(h) a combination of a Group 10 element of the Periodic Table of the Elements or compound thereof and a Group 11 element of the Periodic Table of Elements or a compound thereof;

(i) a combination of plural Group 9 elements of the Periodic Table of Elements having different valencies or compounds thereof.

7. An oxidation catalytic system according to claim 1, wherein said co-catalyst contains plural elements selected from the group consisting of Ti, Zr, V, Cr, Mo, W, Mn, Fe, Ru, Co, Rh, Ni and Cu.

8. An oxidation catalytic system according to claim 1, wherein the ratio of said co-catalyst relative to said imide compound is in a range of 0.1 mole % to not more than 10 mole %.

9. A process for oxidation which comprises a step of contacting a substrate with oxygen in the presence of an oxidation catalytic system claimed in claim 1.

10. A process for oxidation according to claim 9, wherein said substrate is at least one member selected from the group consisting of a hydrocarbon, a heterocyclic compound, an alcohol, an ether, an ester, a ketone, an aldehyde and an amine.

11. A process for oxidation according to claim 9, wherein said substrate is at least one member selected from the group consisting of (a) a cycloalkane, (b) a cycloalkene, (c) a polycyclic hydrocarbon having a methylidyne group as a constitutive element of the ring, (d) an aromatic compound having a methyl group or methylene group in an adjacent position of an aromatic ring and (e) a conjugate compound.

12. A process for producing an oxide, which comprises a step of contacting a substrate with oxygen in the presence of an oxidation catalytic system claimed in claim 1 to produce the corresponding ketones, alcohols, aldehydes or carboxylic acids.

* * * * *